United States Patent [19]

Burton et al.

[11] Patent Number: 5,223,610
[45] Date of Patent: Jun. 29, 1993

[54] CHOLERA TOXIN GENE REGULATED BY GROWTH HORMONE PROMOTER

[75] Inventors: Frank H. Burton, San Diego; J. Gregor Sutcliffe, Cardiff-By-The-Sea, both of Calif.

[73] Assignee: The Scripps Research Institute, La Jolla, Calif.

[21] Appl. No.: 528,852

[22] Filed: May 18, 1990

[51] Int. Cl.$^5$ .............................. C12N 15/31
[52] U.S. Cl. .................... 536/24; 435/69.2; 435/172.3; 435/320.1
[58] Field of Search ............ 536/27; 435/172.3, 320.1, 435/69.2

[56] References Cited

PUBLICATIONS

Behringer et al. (1988), Genes & Dev., vol. 2(4), pp. 453-461, (Chem. Abstracts, vol. 109, 180607).
Mekalanos et al., (Dec., 1983), Nature, vol. 306, pp. 551-557.
Behringer et al., Genes & Dev., 2:453-461 (1988).
Palmiter et al., Cell, 50:435-443 (1988).
Brinster et al., Cell, 27:223-231 (1981).

*Primary Examiner*—Richard A. Schwartz
*Assistant Examiner*—Philip W. Carter
*Attorney, Agent, or Firm*—Douglas A. Bingham; Thomas Fitting; April C. Logan

[57] ABSTRACT

The present invention contemplates a method of physiologic engineering by genetically altering second messenger levels in cells. This method allows the hyperactivation or inhibition of cell function within cells, tissues and animals by introducing a foreign gene that alters a second messenger system. The use of physiologically engineered animals as systems for determining the effectiveness of therapeutic compositions is also contemplated.

1 Claim, 13 Drawing Sheets

TCGAGTCAGAGCAATCCGAGCCTCAGTCAAAGGCTACTGTTGGGAATGCTGTCGGGACCAAGGCGGTTGCTCC

TGCGTGTTTGGTTTTTTTGTATTGGTCGGCTTTGTGTCCAAGATGGTTTTGTCACTGTTGGTGATGAGCGTTATCGCC

TCGTAGACAATTTGGACATTCCTTATCGTGGTCTATGGGCGACAGGTCATCACATTTACAAGGATACGCTTACA

GTGTTTTTTGAAACCGAGAGT.GGCAGCGTCCCAACAGAGCTGTTTGCATCAGGCTACCGCTACAAGGTGCTACCGT

TACCGGATTTTAATCACTTTGTGGTGTTCGATACCTTTGCAGCGCAAGGCTGTGGGTAGAAGTGAAACGGGGTT

```
                                                            A GAT GACATCA GTTGCAT
TACCGATAAAAACAGAAAATGATAAAAAAGGACTAAATAGTATATTTTGATTTTTGATTTTTGATTTCAAATAATA

GGTTAGATAAA  AAG GGTTA C   CCGGATTG C  C G A G T T T A TTTTCC CG      AA
CAAATTTATTTACTTATTTAATTGTTTTGATCAATTATTTTCTGTTAAACAAAGGGAGCATTAT ATG GTA
                                                                 Met Val
                                                                     Lys
                                                                     18

T     CT  C A T          A    G   G CCA  T              GC C
AAG ATA ATA TTT GTG TTT TTT ATT TTC TTA TCA TCA TTT TCA TAT GCA AAT GAT GAT
Lys Ile Ile Phe Val Phe Phe Ile Phe Leu Ser Ser Phe Ser Tyr Ala Asn Asp Asp
Asn     The     Ile             Leu     Ala     Pro Leu                 Gly
                                                                      1
```

FIG.IA

```
                                    600
                                   XbaI
    GA      C    T    T    C           C    A              A   GT   TC   C G  A
    .                .                 .              .                   .
    AAG TTA TAT CGG GCA GAT TCT AGA CCT CCT GAT GAA ATA AAG CAG TCA GGT GGT
    Lys Leu Tyr Arg Ala Asp Ser Arg Pro Pro Asp Glu Ile Lys Gln Ser Gly Gly
    Arg                                                     Arg Phe Arg Ser
                             10                                        20

.C        T A T              . C   T A   .A                T · T
    CCT ATG CCA AGA GGA CAG AGT GAG TAC TTT GAC CGA GGT ACT CAA ATG AAT ATC AAC
    Leu Met Pro Arg Gly Gln Ser Glu Tyr Phe Asp Arg Gly Thr Gln Met Asn Ile Asn
                        Asn
                              30                                         40

700
           C   G         A    A    C         C   A T T         C
    .            .              .              .              .
    CTT TAT GAT CAT GCA AGA GGA ACT CAG ACG GGA TTT GTT AGG CAC GAT GAT GAA
    Leu Tyr Asp His Ala Arg Gly Thr Gln Thr Gly Phe Val Arg His Asp Asp Gly
                                                                Tyr
                           50

800
        .   T   T C.              .   T    .   CA   A   .G TA              A
    TAT GTT TCC ACC TCA ATT AGT TTG AGA AGT GCC CAC TTA GTG GGT CAA ACT ATA TTG
    Tyr Val Ser Thr Ser Ile Ser Leu Arg Ser Ala His Leu Val Gly Gln Thr Ile Leu
                        Leu                              Ala        Ser
     60                                              70

A   A T    TCA CTT ACT ATA TAT ATC GTT        A   A
     .          .              .              .              .
    TCT GGT CAT TCT ACT TAT TAT ATA TAT GTT ATA GCC ACT GCA CCC AAC ATG TTT
    Ser Gly His Ser Thr Tyr Tyr Ile Tyr Val Ile Ala Thr Ala Pro Asn Met Phe
             Tyr     Leu Thr Ile Tyr Ile               Asn
```

FIG.1B

```
                                                      900
     T           A T A C  T         C        C      T       G  G      A
     .                 .           .            .          .          .
AAC GTT AAT GAT GTA TTA GGG GCA TAC AGT CCT CAT CCA GAT GAA CAA GAA GTT TCT
Asn Val Asn Asp Val Leu Gly Ala Tyr Ser Pro His Pro Asp Glu Gln Glu Val Ser
                    Ile Ser Val                     Tyr
               100                                         110

G           A  A       T  T  G                     T     A
     .           .          .         .         .          .
GCT TTA GGT GGG ATT CCA TAC TCC CAA ATA TAT GGA TGG TAT CGA GTT CAT TTT
Ala Leu Gly Gly Ile Pro Tyr Ser Gln Ile Tyr Gly Trp Tyr Arg Val His Phe
                                                                   Asn
                    120                                    130

1000
     T     A          G              C A   AA   T       C C G            A
     .            .           .             .           .           .
GGG GTG CTT GAT GAA CAA TTA CAT CGT AAT AGG GGC TAC AGA GAT AGA TAT TAC AGT
Gly Val Leu Asp Glu Gln Leu His Arg Asn Arg Gly Tyr Arg Asp Arg Tyr Tyr Ser
        Ile         Arg                         Glu                     Arg
                        140                                    150

T C G A    A     G     AG           C A    A              A
     .            .           .            .           .
AAC TTA GAT ATT GCT CCA GCA GCA GAT GGT TAT GGA TTG GCA GGT TTC CCT CCG
Asn Leu Asp Ile Ala Pro Ala Ala Asp Gly Tyr Gly Leu Ala Gly Phe Pro Pro
            Asn             Glu                Arg
                            160

1100
     T   C CA          A      A   C                   A  AA       T   A
     .           .           .            .           .           .
GAG CAT AGA GCT TGG AGG GAA GAG CCG TGG ATT CAT CAT GCA CCG CCG GGT TGT GGG
Glu His Arg Ala Trp Arg Glu Glu Pro Trp Ile His His Ala Pro Pro Gly Cys Gly
Asp     Gln                                                           Gln
170                                        180
```

FIG.IC

```
       G  T A T       A    ATC  CA G    G           T A      G G G      C G  AT    G
      AAT GCT CCA AGA TCA TCG ATG AGT AAT ACT TGC GAT GAA AAA ACC CAA AGT CTA
      Asn Ala Pro Arg Ser Ser Met Ser Asn Thr Cys Asp Glu Lys Thr Gln Ser Leu
      Asp Ser Ser     Thr Ile Thr Gly Asp         Asn     Glu         Asn
              190                     200

1200
      A C  AC    T    AT  C  AGG       T       A          G  G   G                 A
      GGT GTA AAA TTC CTT GAC GAA TAC CAA TCT AAA GTT AAA AGA CAA ATA TTT TCA GGC
      Gly Val Lys Phe Leu Asp Glu Tyr Gln Ser Lys Val Lys Arg Gln Ile Phe Ser Gly
      Ser Thr Ile Tyr     Arg                                                  Asp
                  210                                 220

1300
              G   A   G G     C  T  T     C         CG              A      G
      TAT CAA TCT GAT ATT GAT ACA CAT AAT AGA ATT AAG GAT GAA TTA TGATT AAA TTA
      Tyr Gln Ser Asp Ile Asp Thr His Asn Arg Ile Lys Asp Glu Leu
                      Glu Val     Ile Tyr             Arg         Met Ile Lys Leu
                          230                                         Asn     Val
                                                                  240
                                                                     21

G   TA       A        G  CG        C   T  CT           C     G T
             AAA TTT GGT GTT TTT TTT ACA GTT TTA CTA TCT TCA GCA TAT GCA CAT GGA ACA
             Lys Phe Gly Val Phe Phe Thr Val Leu Leu Ser Ser Ala Tyr Ala His Gly Thr
                 Cys Tyr     Leu         Ala                     Leu             Ala
                                          10                                     + 1

1400
                 C   G  C         A C A C A    T G      AT  G
             CCT CAA AAT ATT ACT GAT TTG TGT GCA GAA TCA CAC AAC ACA CAA ATA TAT ACG
             Pro Gln Asn Ile Thr Asp Leu Cys Ala Glu Ser His Asn Thr Gln Ile Tyr Thr
                     Thr             Glu     Ser         Arg                  (his)
                                              10
```

FIG.ID

```
       A        C         C A     A        G        G A G  A    C           A      T
       .                 .                 .                 .                 .
CTA AAT GAT AAG ATA TTT TCG TAT ACA GAA TCT CTA GCT GGA AAA AGA GAG ATG GCT
Leu Asn Asp Lys Ile Phe Ser Tyr Thr Glu Ser Leu Ala Gly Lys Arg Glu Met Ala
Ile     (Asn)           Leu                     Met                         Val
 20                                      30
                                      1500
                A     T    GC   C   A    CA        G   C       C   G G C
                .                 .                 .                 .
ATC ATT ACT TTT AAG AAT GGT GCA ATT TTT CAA GTA GAA GTA CCA AGT AGT CAA
Ile Ile Thr Phe Lys Asn Gly Ala Ile Phe Gln Val Glu Val Pro Ser Ser Gln
                Met Ser         Glu(Thr)                          (Gly)
         40                                      50
             C   C   G               C                     C  A T A  A  C A
                .                 .                 .                 .
CAT ATA GAT TCA CAA AAA AAA GCG ATT GAA AGG ATG AAG GAT ACC CTG AGG ATT GCA
His Ile Asp Ser Gln Lys Lys Ala Ile Glu Arg Met Lys Asp Thr Leu Arg Ile Ala
                                                        (Asn)               Thr
             60                                      70
                                      1600
       G   C   G AC       A T   T   A                     C              C   C
                .                 .                 .                 .
TAT CTT ACT GAA GCT AAA GTC GAA AAG TTA TGT GTA TGG AAT AAT AAA ACG CCT
Tyr Leu Thr Glu Ala Lys Val Glu Lys Leu Cys Val Trp Asn Asn Lys Thr Pro
                Thr         Ile Asp
                 80                                      90
 A   T A       G        C         AA    C   G
    .                 .                 .                 .
CAT GCG ATT GCC GCA ATT AGT ATG GCA AAT TAA GATATAAAAAGCCCACCTCAGTGGGCTTTTT
His Ala Ile Ala Ala Ile Ser Met Ala Asn
Asn Ser                         Lys
                           100    103

1700
    .                 .                 .                 .                 .
TGTGGTTCGATGATGAGAAGCAACCGTTTTGCCCAAACATGTATTACTGCAAGTATGATGTTTTTATTCCA
```

FIG. IE

```
                                   1800
     .         .         .         .         .         .         .         .
CATCCTTAGTGCGTATTATGTGGCGCGGCATTATGTTGAGGGGCAGTCGTCAGTACCATTGCGCCAGCACTGACGG

1900
     .         .         .         .         .         .         .         .
CCTCACTTGCAGCAGAACGTGGGCAGCTTGCTGAATCGTTCTGCAAGAGTGAGCCCGTAACATAATGGCGT

.         .         .         .         .         .         .         .
ATAATACGCATTAAGGCGGTATGTCATTTCGGTATGTCAAAAATGACATAATTCGATTTATTCTGATTCCAGCCGT

2000
     .         .         .         .
CCGCCGCAGTCATCAGCTTCGCTGATGCGAGG
```

FIG. IF

```
EcoRI
GAATTCGTCGCCTCGCCCTGGTTCGCCGTCATGGCCCCCAAGGGAACCGACCCCAAGATA
                                        100
ATCGTCCTGCTCAACCGCCACATCAACGAGGCGCTGCAGTCCAAGGCGGTCGTCGAGGCC
TTTGCCGCCCAAGGCGCCACGCCGGTCATCGCCACGCCGGATCAGACCCGCGGCTTCATC
           200
GCAGACGAGATCCAGCGCTGGGCCGGCGTCGTGCGCGAAACCGGCGCCAAGCTGAAGTAG
                                                          300
CAGCGCAGCCCTCCAACGCGCCATCCCCGTCCGGCCGGCACCATCCCGCATACGTGTTGG
CAACCGCCAACGCGCATGCGTGCAGATTCGTCGTACAAACCCTCGATTCTTCCGTACAT
                                 400
CCCGCTACTGCAATCCAACACGGCATGAACGCTCCTTCGGCGCAAAGTCGCGCGATGGTA
                         -35                           -10
CCGGTCACCGTCCGGACCGTGCTGACCCCCCTGCCATGGTGTGATCCGTAAAATAGGCAC
                   500        S1
CATCAAAACGCAGAGGGGAAGACGGGATGCGTTGCACTCGGGCAATTCGCCAAACCGCAA
↑                             fM  R  C  T  R  A  I  R  Q  T  A
                                                          600
GAACAGGCTGGCTGACGTGGCTGGCGATTCTTGCCGTCACGGCGCCCGTGACTTCGCCGG
 R  T  G  W  L  T  W  L  A  I  L  A  V  T  A  P  V  T  S  P
CATGGGCCGACGATCCTCCCGCCACCGTATACCGCTATGACTCCCGCCCGCCGGAGGACG
 A  W  A  *  D  D  P  P  A  T  V  Y  R  Y  D  S  R  P  P  E  D
                                 700
TTTTCCAGAACGGATTCACGGCGTGGGGAAACAACGACAATGTGCTCGACCATCTGACCG
 V  F  Q  N  G  F  T  A  W  G  N  N  D  N  V  L  D  H  L  T
GACGTTCCTGCCAGGTCGGCAGCAGCAACAGCGCTTTCGTCTCCACCAGCAGCAGCCGGC
 G  R  S  C  Q  V  G  S  S  N  S  A  F  V  S  T  S  S  S  R
           800
GCTATACCGAGGTCTATCTCGAACATCGCATGCAGGAAGCGGTCGAGGCCGAACGCGCCG
 R  Y  T  E  V  Y  L  E  H  R  M  Q  E  A  V  E  A  E  R  A
                                                          900
GCAGGGGCACCGGCCACTTCATCGGCTACATCTACGAAGTCCGCGCCGACAACAATTTCT
 G  R  G  T  G  H  F  I  G  Y  I  Y  E  V  R  A  D  N  N  F
ACGGCGCCGCCAGCTCGTACTTCGAATACGTCGACACTTATGGCGACAATGCCGGCCGTA
 Y  G  A  A  S  S  Y  F  E  Y  V  D  T  Y  G  D  N  A  G  R
                                 1000
TCCTCGCCGGCGCGCTGGCCACCTACCAGAGCGAATATCTGGCACACCGGCGCATTCCGC
 I  L  A  G  A  L  A  T  Y  Q  S  E  Y  L  A  H  R  R  I  P
CCGAAAACATCCGCAGGGTAACGCGGGTCTATCACAACGGCATCACCGGCGAGACCACGA
 P  E  N  I  R  R  V  T  R  V  Y  H  N  G  I  T  G  E  T  T
           1100
CCACGGAGTATTCCAACGCTCGCTACGTCAGCCAGCAGACTCGCGCCAATCCCAACCCCT
 T  T  E  Y  S  N  A  R  Y  V  S  Q  Q  T  R  A  N  P  N  P
```

FIG.2A

```
                                                        1200
ACACATCGCGAAGGTCCGTAGCGTCGATCGTCGGCACATTGGTGCATGGCGCCGGTGATA
 Y  T  S  R  R  S  V  A  S  I  V  G  T  L  V  H  G  A  G  D

GCGCTTGCATGGCGCGGCAGGCCGAAAGCTCCGAGGCCATGGCAGCCTGGTCCGAACGCG
 S  A  C  M  A  R  Q  A  E  S  S  E  A  M  A  A  W  S  E  R
                                    1300
CCGGCGAGGCGATGGTTCTCGTGTACTACGAAAGCATCGCGTATTCGTTCTAGACCTGGC
 A  G  E  A  M  V  L  V  Y  Y  E  S  I  A  Y  S  F  U
                                       S2
CCAGCCCCGCCCAACTCCGGTAATTGAACAGCATGCCGATCGACCGCAAGACGCTCTGCC
                               fM  P  I  D  R  K  T  L  C
          1400
ATCTCCTGTCCGTTCTGCCGTTGGCCCTCCTCGGATCTCACGTGGCGCGGGCCTCCACGC
 H  L  L  S  V  L  P  L  A  L  L  G  S  H  V  A  R  A *S  T
                                                        1500
CAGGCATCGTCATTCCGCCGCAGGAACAGATTACCCAGCATGGCAGCCCCTATGGACGCT
 P  G  I  V  I  P  P  Q  E  Q  I  T  Q  H  G  S  P  Y  G  R

GCGCGAACAAGACCCGTGCCCTGACCGTGGCGGAATTGCGCGGCAGCGGCGATCTGCAGG
 C  A  N  K  T  R  A  L  T  V  A  E  L  R  G  S  G  D  L  Q
                                  1600
AGTACCTGCGTCATGTGACGCGCGGCTGGTCAATATTTGCGCTCTACGATGGCACCTATC
 E  Y  L  R  H  V  T  R  G  W  S  I  F  A  L  Y  D  G  T  Y

TCGGCGGCGAATATGGCGGCGTGATCAAGGACGGAACACCCGGCGGCGCATTCGACCTGA
 L  G  G  E  Y  G  G  V  I  K  D  G  T  P  G  G  A  F  D  L
              1700
AAACGACGTTCTGCATCATGACCACGCGCAATACGGGTCAACCCGCAACGGATCACTACT
 K  T  T  F  C  I  M  T  T  R  N  T  G  Q  P  A  T  D  H  Y
                                                     1800
ACAGCAACGTCACCGCCACTCGCCTGCTCTCCAGCACCAACAGCAGGCTATGCGCGGTCT
 Y  S  N  V  T  A  T  R  L  L  S  S  T  N  S  R  L  C  A  V

TCGTCAGAAGCGGGCAACCGGTCATTGGCGCCTGCACCAGCCCGTATGACGGCAAGTACT
 F  V  R  S  G  Q  P  V  I  G  A  C  T  S  P  Y  D  G  K  Y
                                1900
GGAGCATGTACAGCCGGCTGCGGAAAATGCTTTACCTGATCTACGTGGCCGGCATCTCCG
 W  S  M  Y  S  R  L  R  K  M  L  Y  L  I  Y  V  A  G  I  S

TACGCGTCCATGTCAGCAAGGAAGAACAGTATTACGACTATGAGGACGCAACGTTCGAGA
 V  R  V  H  V  S  K  E  E  Q  Y  Y  D  Y  E  D  A  T  F  E
                     2000
CTTACGCCCTTACCGGCATCTCCATCTGCAATCCTGGATCATCCTTATGCTGAGACGCTT
 T  Y  A  L  T  G  I  S  I  C  N  P  G  S  S  L  C  U
                                                S4     2100
CCCCACTCGAACCACCGCCCCGGGACAGGGCGGCGCCCGGCGGTCGCGCGTGCGCGCCCT
                                              fM  R  A  L
```

FIG. 2B

```
GGCGTGGTTGCTGGCATCCGGCGCGATGACGCATCTTTCCCCCGCCCTGGCCGACGTTCC
 A  W  L  L  A  S  G  A  M  T  H  L  S  P  A  L  A  * D  V  P
                                       2200
TTATGTGCTGGTGAAGACCAATATGGTGGTCACCAGCGTAGCCATGAAGCCGTATGAAGT
 Y  V  L  V  K  T  N  M  V  V  T  S  V  A  M  K  P  Y  E  V
CACCCCGACGCGCATGCTGGTCTGCGGCATCGCCGCCAAACTGGGCGCCGCGGCCAGCAG
 T  P  T  R  M  L  V  C  G  I  A  A  K  L  G  A  A  A  S  S
                    2300
CCCGGACGCGCACGTGCCGTTCTGCTTCGGCAAGGATCTCAAGCGTCCCGGCAGCAGTCC
 P  D  A  H  V  P  F  C  F  G  K  D  L  K  R  P  G  S  S  P
                                                          2400
CATGGAAGTCATGTTGCGCGCCGTCTTCATGCAACAACGGCCGCTGCGCATGTTTCTGGG
 M  E  V  M  L  R  A  V  F  M  Q  Q  R  P  L  R  M  F  L  G
TCCCAAGCAACTCACTTTCGAAGGCAAGCCCGCGCTCGAACTGATCCGGATGGTCGAATG
 P  K  Q  L  T  F  E  G  K  P  A  L  E  L  I  R  M  V  E  C
CAGCGGCAAGCAGGATTGCCCCTGAAGGCGAACCCCATGCATACCATCGCATCCATCCTG
 S  G  K  Q  D  C  P  U       fM  H  T  I  A  S  I  L
TTGTCCGTGCTCGGCATATACAGCCCGGCTGACGTCGCCGGCTTGCCGACCCATCTGTAC
 L  S  V  L  G  I  Y  S  P  A  D  V  * A  G  L  P  T  H  L  Y
              2600
AAGAACTTCACTGTCCAGGAGCTGGCCTTGAAACTGAAGGGCAAGAATCAGGAGTTCTGC
 K  N  F  T  V  Q  E  L  A  L  K  L  K  G  K  N  Q  E  F  C
                                                          2700
CTGACCGCCTTCATGTCGGGCAGAAGCCTGGTCCGGGCGTGCCTGTCCGACGCGGGACAC
 L  T  A  F  M  S  G  R  S  L  V  R  A  C  L  S  D  A  G  H
GAGCACGACACGTGGTTCGACACCATGCTTGGCTTTGCCATATCCGCGTATGCGCTCAAG
 E  H  D  T  W  F  D  T  M  L  G  F  A  I  S  A  Y  A  L  K
                                        2800
AGCCGGATCGCGCTGACGGTGGAAGACTCGCCGTATCCGGGCACTCCCGGCGATCTGCTC
 S  R  I  A  L  T  V  E  D  S  P  Y  P  G  T  P  G  D  L  L
GAACTGCAGATCTGCCCGCTCAACGGATATTGCGAATGAACCCTTCCGGAGGTTTCGACG
 E  L  Q  I  C  P  L  N  G  Y  C  E  U
                2900
TTTCCGCGCAATCCGCTTGAGACGATCTTCCGCCCTGGTTCCATTCCGGGAACACCGCAA
                                                         3000
CATGCTGATCAACAACAAGAAGCTGCTTCATCACATTCTGCCCATCCTGGTGCTCGCCCT
 fM  L  I  N  N  K  K  L  L  H  H  I  L  P  I  L  V  L  A  L
GCTGGGCATGCGCACGGCCCAGGCCGTTGCGCCAGGCATCGTCATCCCGCCGAAGGCACT
 L  G  M  R  T  A  Q  A  * V  A  P  G  I  V  I  P  P  K  A  L
```

FIG. 2C

```
                                      3100
GTTCACCCAACAGGGCGGCGCCTATGGACGCTGCCCGAACGGAACCCGCGCCTTGACCGT
 F  T  Q  Q  G  G  A  Y  G  R  C  P  N  G  T  R  A  L  T  V

GGCCGAACTGCGCGGCAACGCCGAATTGCAGACGTATTTGCGCCAGATAACGCCCGGCTG
 A  E  L  R  G  N  A  E  L  Q  T  Y  L  R  Q  I  T  P  G  W
                  3200
GTCCATATACGGTCTCTATGACGGTACGTACCTGGGCCAGGCGTACGGCGGCATCATCAA
 S  I  Y  G  L  Y  D  G  T  Y  L  G  Q  A  Y  G  G  I  I  K
                                                        3300
GGACGCGCCGCCAGGCGCGGGGTTCATTTATCGCGAAACTTTCTGCATCACGACCATATA
 D  A  P  P  G  A  G  F  I  Y  R  E  T  F  C  I  T  T  I  Y

CAAGACCGGGCAACCGGCTGCGGATCACTACTACAGCAAGGTCACGGCCACGCGCCTGCT
 K  T  G  Q  P  A  A  D  H  Y  Y  S  K  V  T  A  T  R  L  L
                                3400
CGCCAGCACCAACAGCAGGCTGTGCGCGGTATTCGTCAGGGACGGGCAATCGGTCATCGG
 A  S  T  N  S  R  L  C  A  V  F  V  R  D  G  Q  S  V  I  G

AGCCTGCGCCAGCCCGTATGAAGGCAGGTACAGAGACATGTACGACGCGCTGCGGCGCCT
 A  C  A  S  P  Y  E  G  R  Y  R  D  M  Y  D  A  L  R  R  L
          3500
GCTGTACATGATCTATATGTCCGGCCTTGCCGTACGCGTCCACGTCAGCAAGGAAGAGCA
 L  Y  M  I  Y  M  S  G  L  A  V  R  V  H  V  S  K  E  E  Q
                                                    3600
GTATTACGACTACGAGGACGCCACATTCCAGACCTATGCCCTCACCGGCATTTCCCTCTG
 Y  Y  D  Y  E  D  A  T  F  Q  T  Y  A  L  T  G  I  S  L  C

CAACCCGGCAGCGTCGATATGCTGAGCCGCCGGCTCGGATCTGTTCGCCTGTCCATGTTT
 N  P  A  A  S  I  C  U
                          3700
TTCCTTGACGGATACCGCGAATGAATCCCTTGAAAGACTTGAGAGCATCGCTACCGCGCC

TGGCCTTCATGGCAGCCTGCACCCTGTTGTCCGCCACGCTGCCCGACCTCGCCCAGGCCG
                3800
GCGGCGGGCTGCAGCGCTGTCAACCACTTCATGGCGAGCATCGTGGTCGTACTGCCGCGG
                                                        3900
CGGTCAGTGGCCACGGTGACCATCGCCATAATCTGGGCGGGCTACAAGCTGCTGTTCCGG

CACGCCGATGTGCTGGACGTGGTGCGTGTGGTGCTGGCGGGAGCTGCTGATCGGCGCATC
                                    4000
GGCCGAAATCGCTCGTTATCTGCTGACCTGAATCCTGGACGTATCGAACATGCGTGATCC

GCTTTTCAAGGGCTGCACCCGGCGCCGCGATGCTGATGGCGTACCCGCCACGGCAGGCCG
                  4100
TGTGCAGCCGGCACCATTCCCTGCTGGGCCATCTCGGTTCAGCATCCGCTTTCTGGCCTT
                                                      4200
GTTTCCCGTGGCATTGCTGGCGATGCGGATCATGATCCGGCGCGATGACCAGCAGTTCCG
    Sau3A
CCTGATC
```

FIG. 2D

CHOLERA TOXIN GENE REGULATED BY GROWTH HORMONE PROMOTER

This invention was made with government support under Government Contracts GM 32355 and NS 22111. The government has certain rights in the invention.

TECHNICAL FIELD

The present invention relates to a method for preparing cells, tissues and animals having an altered second messenger level and the use of these animals to determine the therapeutic or carcinogenic potential of a composition.

BACKGROUND

Cells communicate with each other by a variety of signal molecules, such as neurotransmitters, hormones and growth factors that are detected by specific receptors on the plasma membrane of the responding cell. Stimulation of a receptor by its agonist initiates a series of biochemical processes that produce an intracellular signal called a second messenger. This second messenger ultimately causes a change in the behavior of an cell resulting in a biological response such as secretion of an enzyme, contraction or initiation of cell division.

The cyclic nucleotides cyclic adenine monophosphate (cAMP) and cyclic guanine monophosphate (cGMP) act as second messengers in many cell types to couple extracellular stimulatory or inhibitory signals with the appropriate cellular physiological responses. Examples of important cellular physiological responses that are regulated by cyclic nucleotide second messengers include visual excitation, activation of adenylate cyclase and growth hormone secretion by growth hormone releasing factor, regulation of ion channels by neurotransmitters and membrane receptor activation and olfaction. See, for example, Gilman, *Ann. Rev. Biochem.,* 56:615–49 (1987); Neer et al., *Nature,* 333:129–134 (1988); Vallar et al., *Nature,* 330:566–568 (1987); Dolphin, *Trends in Neurosciences, Volume* 10, February (1987); and Stryer, *Ann. Rev. Neurosci.,* 9:87–119 (1986).

The hormone-responsive tissues are the most extensively studied examples of regulation of physiological responses by cyclic nucleotides. For example, growth hormone releasing factor (GRF) is produced by the hypothalamus, and binds to a receptor on growth hormone (GH)-producing pituitary somatotrope cells. This binding causes stimulation of the ubiquitous receptor-associated G-protein $G_s$, leading to activation of adenylate cyclase which in turn causes the elevation of cAMP levels within the somatotrope cells. Bilezikjian et al., *Endocrinology.* 113 1726–1731 (1983) and Vallar et al., *Nature,* 330:566–568 (1987). The elevated cAMP levels within the somatotrope cells increases the rate of growth hormone gene transcription and consequently the secretion of growth hormone from the somatotrope cells. Schofield, *Nature,* 215:1382–1383 (1967) and Barinaga et al., *Nature,* 314:279–281 (1985). The somatotrope cells also proliferate in response to the elevated cAMP level. Billesterup et al., *Proc. Natl. Acad. Sci., U.S.A.* 83:6854–6857 (1986). Other G-protein dependent cascades with different specific stimulatory or inhibitory outcomes are found in other hormone-responsive tissues such as the adrenal cortex, thyroid and gonads, as well as in various subsets of neurotransmitter- or light-responsive neurons such as the retinal photoreceptors.

Several bacterial toxins are known to perturb the level of second messengers in cells. See for example, Gill et al., *J. Infect. Dis.,* 133:S103–S107 (1976); Gill et al., *Proc. Natl. Acad. Sci., U.S.A.,* 1975:3050–054 (1978); Katada et al., *J. Biol. Chem.,* 257:7210 (1982). These bacterial toxins activate or inactivate the G-proteins by catalyzing the transfer of an adenosine diphosphate (ADP) ribose group from nicotinamide adenine dinucleotide (NAD) to an amino acid located in or near with the guanine triphosphate (GTP) binding site of the G-protein. Dolphin, *Trends in Neurosciences,* 10:53–57 (1987). Since the toxins act enzymatically, the entry of a single toxin molecule into the cell can, in principle, ADP-ribosylate all of its substrates within the cell. Yamiazumi et al., *Cell,* 15:245–250 (1978). Examples of G-protein ribosylating toxins include the exotoxins from *Escherichia coli. Vibrio cholera,* and *Bordetella pertussis.* Pappenheimer, *J. Hyg.,* 93:397–404 (1984).

All of these toxins together with several other plant and bacterial toxins appear to have a similar structure, consisting of at least one A chain disulfide-linked to at least one B chain. The B-chains bind to specific glycoprotein receptors on the cell surface and allow entry of the A-chain which contains the enzymatic activity into the cell. Ui et al., in *Pertussis Toxin,* Sekura et al., eds., 19–43, Academic Press, San Diego (1985) and Gill, *Proc. Natl. Acd. Sci. U.S.A.,* 72:2064–2068 (1975).

Recent advances in transformation technology allow the introduction of a specific gene sequence into the germ-line of mammals. For review, see Palmiter and Brinster, *Ann. Rev. Genet.,* 20:465–499 (1986). The genes introduced using this technology are integrated into the germ-line and therefore pass from one generation of the next. These techniques have been used to express a variety of end product proteins, such as hormones and to specifically kill certain cells within the developing mammal. Evans et al., U.S. Pat. No. 4,870,009, Sep. 26 (1989); and Palmiter et al., *Cell,* 50:435–443 (1987).

However, the transgenic mammals produced to date have expressed only end product proteins such as hormones, immunoglobulins, and other structural proteins. Expression of these and similar products only allows the elevation of one protein product or the elevation of a series of products within a given biochemical pathway of the cells within the transgenic mouse. Other studies that have specifically killed or ablated a given cell lineage within the transgenic animals have allowed the study of the effects of the cell lineage's absence but do not allow the manipulation of the multiple protein products and the physiology produced from the stimulation of a given cell lineage within the transgenic mouse.

BRIEF SUMMARY OF THE INVENTION

The present invention provides a method of genetically programming an altered second messenger level within the cells or tissues of an animal. The alteration of second messenger levels allows multiple biochemical pathways and entire animal physiology to be modulated.

The method of the present invention for genetically programming a cell includes the steps of introducing into the cell a nucleic acid molecule comprised of a tissue specific promoter operatively linked to (controlling the expression of) a non-lethal modulator gene. The cell is then maintained so the non-lethal modulator gene present on the nucleic acid molecule can be expressed and genetically program the cell.

The present invention also contemplates an isolated nucleic acid comprising a tissue specific promoter controlling the expression of a non-lethal modulator gene and a non-lethal gene under the control of the tissue specific promoter. In preferred embodiments, the non-lethal modulator gene is a non-lethal second messenger system modulator gene or a non-lethal cyclic AMP modulator gene. In other preferred embodiments the non-lethal modulator is a cholera toxin gene or a pertussis toxin gene.

The present invention also contemplates cells, tissues, mammals, and plants containing a nucleic acid molecule of the present invention.

A method for determining the therapeutic effectiveness of a composition by introducing that composition into animals expressing a non-lethal modulator gene in specific tissues is also contemplated.

BRIEF DESCRIPTION OF THE DRAWINGS

FIGS. 1A–1F represent the nucleotide sequence of cholera toxin as determined by Mekalanos et al., *Nature*, 306:551 (1983) is shown.

FIGS. 2A–2D represent the nucleotide sequence of pertussis toxin as determined by Locht et al., *Science*, 232:1558 is shown.

Figure 3:
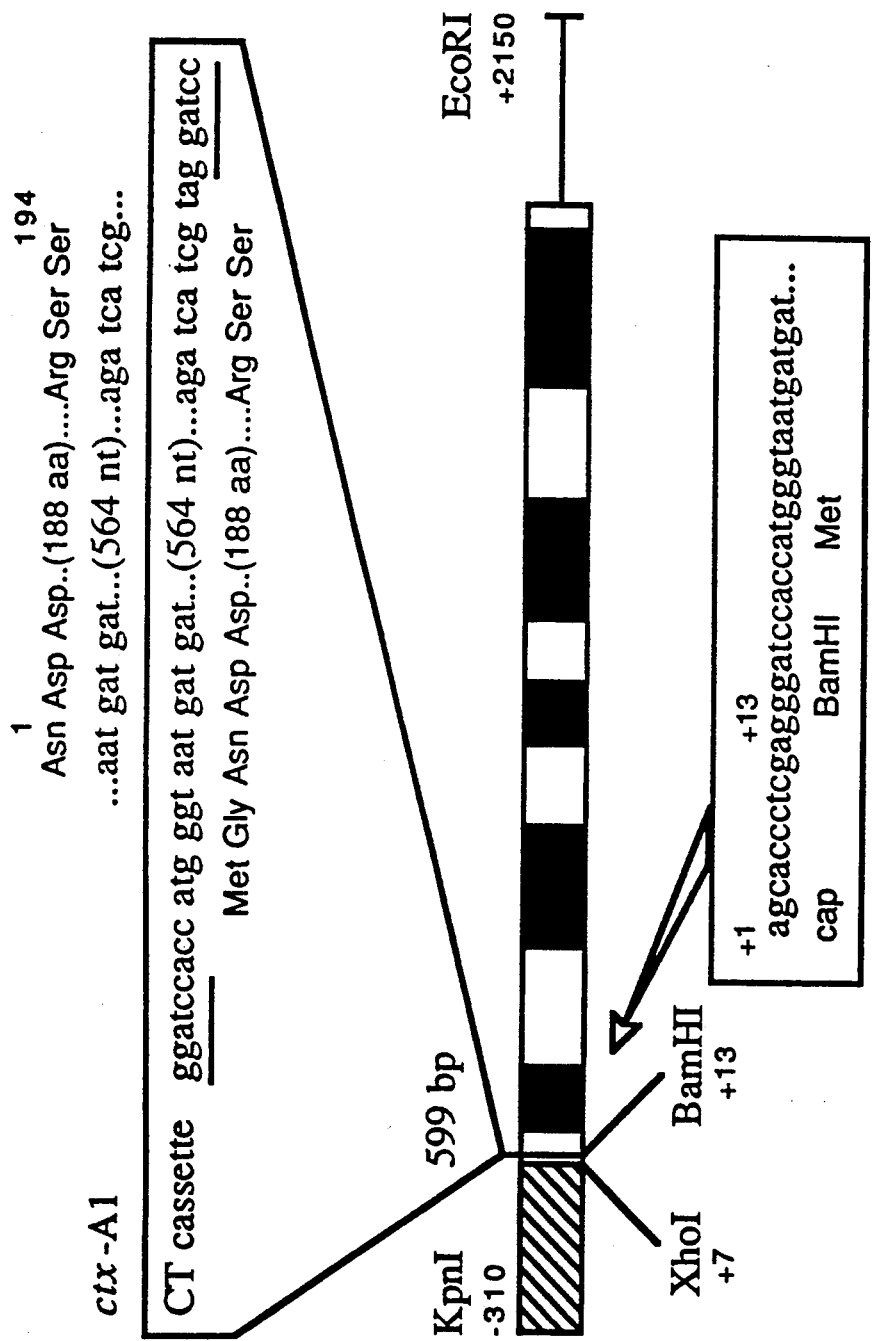
FIG. 3 The details of the construction of the nucleic acid molecule containing the tissue specific rat growth hormone promoter located 5′ of and controlling the expression of the cholera toxin A1 subunit gene are shown. The upper portion of the Figure shows the amino acid and nucleotide sequence of the portion of the cholera toxin (ctx) operon which encodes the mature and enzymatically active intracellular subunit of cholera toxin, A1 described by Mekalanos et at., *Nature*, 306:551–557 (1983), aligned with the nucleotide and predicted amino acid sequence of a PCR-amplified mouse CT cassette. The eukaryotic ATG initiation codon and TAG termination codon in the CT cassette are shown in boldface. The inclusion of the eukaryotic translation initiator, "CCACCATGG", described by Kozak, *Nucleic Acid Research*. 12:857:872 (1984) changes the predicted amino acid sequence of the mouse cholera toxin to add two N-terminal amino acids residues to the ctx-A1 subunit amino acid sequence. The Bam HI restriction endonuclease sites used for placing the cholera toxin cassette under the control of a tissue specific promoter are underlined. The PCR primers used to create the cassette were CT-5. (5′ GCCCGGATCCACCATGGGTAATGAT-GATAAGTTATTTTAT 3′) and CT-3 (5′ GCGGATCCTACGATGATCTTGGAGCATTCC 3′).

The middle portion of the Figure shows the construction of the nucleic acid molecule containing rGH-CT fusion gene by ligation of the 599 bp CT cassette into the BamHI site at position +13 within the 5′ untranslated region of the rat growth hormone/human growth hormone (rGH-hGH) fusion gene that have been previously described by Behringer et al., *Genes and Development*, 2:453–461 (1988). The components of the rGH-hGH fusion gene are: shaded box (rGH promoter and 5′ untranslated region), open boxes (hGH 5′ untranslated region, introns, and 3′ untranslated region) and solid boxes (hGH exons). Insertion of the cassette converts all human sequences into 3′ untranslated sequence. The DNA sequence of the inserted CT cassette and flanking regions within rGH-CT was obtained to confirm error-free PCR amplification and cloning. The sequence of the 5′ untranslated region is shown at bottom. The complete rGH-CT structural gene is carried on a 3 kb KpnI-EcoRI fragment, which was excised from plasmid pUC and used for microinjection.

In FIGS. 4A–4L the pituitary and somatotrope hyperplasia observed in transgenic mice expressing a recombinant nucleic acid molecule containing the tissue specific rat growth hormone promoter controlling the expression of the cholera toxin A1 subunit gene is shown. In FIG. 4A, whole pituitaries of control (left) and transgenic (right) mice. The lesion on the transgenic pituitary was diagnosed as a non-cancerous infarction presumably due to organ compression caused by anterior lobe expansion. In FIGS. 4B–4L the immunohistocytochemical localization of cholera toxin (CT), growth hormone (GH), prolactin (PRL) and thyroid stimulating hormone (TSH) is shown. The pituitaries from transgenic mice expressing the cholera toxin A1 subunit are shown in FIGS. 4C–4G, i, j and l. The pituitaries from control mice are shown in FIGS. 4B, 4H, and 4K.

In FIG. 4C the higher density of GH positive cells in the transgenic mice compared to control mice (FIG. 4B) is shown. In FIGS. 4D–4G, contiguous tissue sections show co-localization of CT (FIG. 4D) with GH (FIG. 4E) positive cells but not with PRL (FIG. 4F) or TSH (FIG. 4G) positive. In FIGS. 4H–4J, PRL staining shows decreased density of PRL positive cells in male (FIG. 4I) but not female (FIG. 4J) transgenics.

In FIGS. 4K and 4L, TSH staining shows equivalent density of TSH positive cells in controls and transgenics.

Pituitaries in FIGS. 4D–4L were prefused with 4% paraformaldehyde and cryostat sectioned. In FIGS. 4B and 4C the pituitaries were fixed in 10% buffered formalin and paraffin sectioned. Formalin fixed sections were pre-treated with sodium borohydride or trypsin to recover staining intensity lessened by formalin-blockage of epitopes. All sections were treated by immunoperoxidase staining with antisera concentrations as follows: anti-rGH (1:2500), anti-CT (1:1000), anti-mPRL (1:500), anti-rTHS (1:500). Couterstaining was used for all sections except those in FIGS. 4B and 4C, where negative cells were visualized and counted by phase contrast.

DETAILED DESCRIPTION OF THE INVENTION

A nucleic acid molecule of the present invention comprises a tissue specific promoter located 5′ of and controlling the expression of a non-lethal modulator gene. The tissue specific promoter is a DNA segment that contains a DNA sequence that control the expression of a gene located 3′ or downstream of the promoter. The promoter is the DNA sequence to which RNA polymerase specifically binds and initiates RNA synthesis (transcription) of that gene, typically located 3′ of the promoter The subject nucleic acid molecule comprises at least 2 different operatively linked DNA segments. The DNA can be manipulated and amplified using the standard techniques described in *Molecular Cloning: A Laboratory Manual*, 2nd Edition, Maniatis et al., eds., Cold Spring Harbor, New York (1989). Typically, to produce a nucleic acid molecule of the present invention, the tissue specific promoter and the non-lethal modulator gene are operatively linked to a vector DNA molecule capable of autonomous replication in a cell. By operatively linking the tissue specific promoter and the non-lethal modulator gene to the vector the attached segments are replicated along with the vector sequences. Thus, a recombinant DNA molecule (rDNA) is a hybrid DNA molecule comprising at least 2 nucleotide sequences not normally found together in nature.

In preferred embodiments, the recombinant nucleic acid molecule that is introduced into the cells of a mammal contains a tissue specific promoter and a non-lethal modulator gene and has had the excess vector sequences removed. These excess vector sequences are removed by cutting the recombinant nucleic acid molecule with 1 or more restriction endonucleases to produce a linear recombinant nucleic acid molecule containing a tissue specific promoter and a non-lethal modulator gene.

The nucleic acid molecule of the present invention is from about 100 base pairs to about 100,000 base pairs in length. Preferably the nucleic acid molecule is from about 50 base pairs to about 50,000 base pairs in length. More preferably the nucleic acid molecule is from about 50 base pairs to about 10,000 base pairs in length. Most preferred is a nucleic acid molecule from about 50 pairs to about 4,000 base pairs in length.

A regulatable promoter is a promoter where the rate of RNA polymerase binding and initiation is modulated by external stimuli. Such stimuli include compositions light, heat, stress and the like. Inducible, suppressible and repressible promoters are regulatable promoters. Tissue specific promoters may also be regulatable promoters. The tissue specific promoter directs the expression of that gene to a specific cell type. The tissue specific promoter causes the gene located 3' of it to be expressed predominantly, if not exclusively in the specific cells where the promoter expressed its endogenous gene. Typically, it appears that if a tissue-specific promoter expresses the gene located 3' of it at all, then it is expressed appropriately in the correct cell types as has been reviewed by Palmiter et al., *Ann. Rev. Genet.*, 20:465–499 (1986). When a tissue specific promoter controlling the expression of a gene, that gene will be expressed in a small number of tissues or cell types rather than in substantially all tissues and cell types. Examples of tissue specific promoters include the immunoglobulin promoter described by Brinster et al., *Nature*, 306:332-336 (1983) and Storb et al., *Nature*, 310:238-231 (1984); the elastase-I promoter described by Swift et al., *Cell*. 38:639-646 (1984); the globin promoter described by Townes et al., *Mol. Cell. Biol.*, 5:1977-1983 (1985), and Magram et al., *Mol. Cell. Biol*, 9:4581-4584 (1989), the insulin promoter described by Bucchini et al., *Proc. Natl. Acad. Sci., U.S.A.*, 83:2511-2515 (1986) and Edwards et al., *Cell*. 58:161 (1989); the immunoglobulin promoter described by Ruscon et al., *Nature*, 314:330-334 (1985) and Grosscheld et al., *Cell*, 38:647-658 (1984); the alpha actin promoter described by Shani, *Mol. Cell. Biol.*, 6:2624-2631 (1986); the alpha crystalline promoter described by Overbeek et al., *Proc. Natl. Acad. Sci. U.S.A.* 82:7815-7819 (1985); the prolactin promoter described by Crenshaw et al., *Genes and Development*, 3:959-972 (1989); the proopiomelanocortin promoter described by Tremblay et al., *Proc. Natl. Acad. Sci., U.S.A.*, 85:8890-8894 (1988); the beta thyroid stimulating hormone (BTSH) promoter described by Tatsumi et al., *Nippon Rinsho*, 47:2213-2220 (1989); the mouse mammary tumor virus (MMTV) promoter described by Muller et al., *Cell*, 54:105 (1988); the albumin promoter described by Palmiter et al., *Ann. Rev. Genet.*, 20:465–499 (1986); the Keratin promoter described by Vassar et al., *Proc.Natl. Acad. Sci., U.S.A.* 86:8565-8569 (1989); the osteonectin promoter described by McVey et al., *J. Biol. Chem.*, 263:11,111-11,116 (1988); the prostate-specific promoter described by Allison et al., *Mol. Cell. Biol.*, 9:2254-2257 (1989); the opsin promoter described by Nathans et al., *Proc. Natl. Acad. Sci., U.S.A.*, 81:4851-4855 (1984); the olfactory marker protein promoter described by Danciger et al., *Proc. Natl. Acad. Sci., U.S.A.*, 86:8565-8569 (1989); the neuron-specific enolase (NSE) promoter described by Forss-Pelter et al., *J. Neurosci. Res.*, 16:141-151 (1986); the L-7 promoter described by Sutcliffe, *Trends in Genetics*, 3:73-76 (1987) and the protamine 1 promoter described Peschon et al., *Ann. New York Acad. Sci.*, 564:186-197 (1989) and Braun et al., *Genes and Development*, 3:793-802 (1989). See Table I for the tissue specificity of the promoters.

TABLE I

| Tissue Specific Promoters | | | |
|---|---|---|---|
| Gene | Species | Tissue Specificity[1] | Ref.[2] |
| α-Actin | Rat | mu, he | A |
| α-Actin | Rat | te, th, lu | A |
| Elastase - 1 | Rat | Pa | B |
| α-Fetoprotein | Mouse | ys, li | C |
| β-Globin | Human | ery | D |
| β-Globin | Rabbit | te, mu | E |
| β-Globin | Rabbit | ery | F |
| τ⁶-Globin | Human | ery | G |
| α¹-Globin | Mouse | br | H |
| Growth hormone | Human | pit | I |
| Immunoglobin-k | Mouse | B | J |
| Immunoglobin-μ | Mouse | B, T | K |
| Insulin | Human | B-cells | L |
| Myosin Light Chain-2 | Rat | mu | M |
| Protamine 1 | Mouse | te | N |
| α-A-crystallin | trans | lens | O |
| Prolactin | | pit | P |
| Proopiomelanocartia | | pit | Q |
| BTSH | | | R |
| MMTV | Mouse | breast | S |
| Albumin | | li | T |
| Keratin | | skin | U |
| Osteonectin | | bone | V |
| Prostate | | prostate | W |
| Olfactory Marker Protein | | neuron | X |
| NSE | | neuron | Y |
| L-7 | | neuron | Z |

TABLE I-continued

| Opsin | retina | A1 |
|---|---|---|

[1] Abbreviations: br, brain; B, lymphocytes; mu, skeletal muscle; he, cardiac muscle; te, testis; beta, beta cells; th, thymus; lu, lung; Pa, exocrine pancreas; ys, yolk sac; li, liver; ery, erythroid cells; pit, pituitary and lens, eye lens.

[2] References:
A - Shani, Mol. Cel. Biol., 6:2624-31 (1986).
B - Swift et al., Cell, 38:639-649 (1984).
C - Krumlauf et al., Nature, 319:224-226 (1985).
D - Townes et al., EMBO J., 4:1715-1723 (1985).
E - Lacy et al., Cell, 34:343-348 (1983).
F - Wagner et al., Proc. Natl. Acad. Sci., USA, 78:6376-6380 (1981).
G - Brinster et al., Nature, 283:499-501 (1980).
H - Rusconi et al., in The Impact of Gene Transfer Techniques in Eukaryotic Cell Biology, ed. J. S. Schell et al., pp 134-152, Berlin: Springer Verlag (1984).
I - Behringer et al., Genes Dev., 2:453 (1988).
J - Storb et al., Nature. 310:238-241 (1984).
K - Grosschedl et al., Cell, 38:647-658 (1984).
L - Selden et al., Nature. 321:545-528 (1986).
M - Shani, Nature, 314:283-286 (1985).
N - Peschon et al., Ann. N. York Acad. Sci., 564:186-197 (1989).
O - Breitman et al., Dev., 106:457-463 (1989).
P - Crenshaw et al., Genes and Development, 3:959-972 (1989).
Q - Tremblay et al., Proc. Natl. Acad. Sci., USA, 85:8890-8894 (1988).
R - Tatsumi et al., Nippon Rinsho, 47:2213-2220 (1989).
S - Muller et al., Cell 54:105 (1988).
T - Palmiter et al., Ann. Rev. Genet., 20:465-499 (1986).
U - Vassar et al., Proc. Natl. Acad. Sci., USA, 86:8565-8569 (1989).
V - McVey et al., J. Biol. Chem., 263:11,111-11,116 (1988).
W - Allison et al., Mol. Cell. Biol., 9:2254-2257 (1989).
X - Danciger et al., Proc. Natl. Acad. Sci., USA, 86:8565-8569 (1989).
Y - Forss-Petter et al., J. Neurosci. Res., 16:141-151 (1986).
Z - Sutcliffe, Trends in Genetics, 3:73-76 (1987).
A1 - Nathans et al., Proc. Natl. Acad. Sci., USA, 81:4851-4855 (1984).

A recombinant nucleic acid molecule of the present invention comprises a non-lethal modulator gene located 3' of the tissue specific promoter. A non-lethal modulator gene of the present invention is a gene that codes for an intracellular modulator that alters a complex biochemical pathway of the cell in which the gene is expressed but is not lethal to that cell. The intracellular modulator of the present invention includes proteins, RNAs and DNAs that are made within a cell and modulate a complex biochemical activity of that same cell by directly altering a biochemical substance or process without first being excreted from that cell. The non-lethal modulator gene is expressed from the tissue-specific promoter located 5' of it and it directly modulates, that is increases or decreases the amount or activity of a biochemical substance or process.

The non-lethal modulator gene codes for an intracellular modulator that effects or alters a complex biochemical pathway. A complex biochemical pathway is a series of biochemical processes that produce or change the amount and/or the activity of several end-product proteins. In a complex biochemical pathway the series of biochemical processes are interconnected in such a way that a change in an early biochemical process or substance results in a regulation of several other biochemical processes or end-products. Examples of complex biochemical pathways include the degradation of glucose by glucolysis and the tricarboxylic acid cycle, the multiple biochemical and physiological effects of an increase in intracellular cyclic AMP levels including increased protein or hormone production, cell development glycogenolysis and reduced glycogen synthesis in liver cells, activation of retinal specific cyclic GMP-phosphodiesterase by light, the activation of phospholipase C the mobilization of intracellular calcium stores triggering of calcium dependent events such as learning, memory and neurotransmitter release. See for example, Schofield, Nature, 215:1382-1383 (1967); Baringa et al., Nature. 314:279-281 (1985); Billestrup et al., Proc. Natl. Acad. Sci. U.S.A., 83:6854-6857 (1986); Gilman, Ann. Rev. Biochem., 56:615-649 (1987); and Biochemistry, Second Edition, Lehninger, North Publishers, New York, N.Y. (1975).

In other preferred embodiments, the recombinant nucleic acid molecule of the present invention comprises a tissue specific promoter located 5' of a non-lethal modulator gene and a non-lethal second messenger system modulator gene. A non-lethal second messenger system modulator gene is a gene that codes for an intracellular modulator that alters a second messenger system of the cell in which the gene is expressed but is not lethal to that cell. In addition, the non-lethal second messenger system modulator gene is not a homolog of a cellular gene within the cell it is introduced into. Examples of homologs of cellular genes include the oncogenes such as fos, myc, neu, and ras. Toxin genes such as the cholera toxin gene, the pertussis toxin gene and the E. coli heat-labile toxin gene do not have cellular homologs in eukaryotic cells.

Second messenger systems present in cells include the cyclic AMP (cAMP) system, the cyclic GMP (cGMP), and the system for synthesis of diacylglycerol and inositol phosphates and which activate protein Kinase C. For review, see Hokin, Ann. Rev. Biochem., 54:205 (1985); Berridge, Ann. Rev. Biochem., 56:159 (1987); and Majerus et al., Science. 234:1519 (1986). Second messengers, once formed, invoke a host of intracellular reactions that eventually lead to many of the cellular processes (complex biochemical events) such as metabolism, excitation, secretion, contraction, sensory mechanism and cell growth and proliferation.

Examples of non-lethal second messenger system modulator genes include the cholera A1 subunit toxin gene described by Mekalanos et al., Nature, 306:551-557 (1983); the gene encoding pertussis toxin S1 subunit described by Locht et al., Science, 232:1258 (1986); the gene encoding E. coli heat-labile toxin described by Dallas et al., J. Bact., 139:850-858 (1979).

In other preferred embodiments a recombinant nucleic acid molecule of the present invention comprises a tissue specific promoter controlling the expression of a non-lethal cholera toxin gene and a cholera toxin gene located 3' of the tissue specific promoter. For example, a non-lethal cholera toxin gene includes the sequence of the cholera toxin gene encoding the A1 polypeptide has been described by Mekalanos et al., Nature, 306:551-557 (1983). The present invention also contemplates a segment of the cholera toxin A1 gene that encodes a polypeptide that is an enzyme that is capable of catalyzing the ADP-ribosylation and activation of $G_s$, the GTP-binding regulatory component that stimulates the adenylate cyclase complex. A cholera toxin gene of the present invention includes those nucleic acid segments that non-randomly hybridize to nucleotides 569 to 1150 of FIGS. 1A-1D or to a complementary strand of nucleotides 569 to 1150 of FIGS. 1A-1D.

In other preferred embodiments, a recombinant nucleic acid molecule of the present invention comprises a tissue specific promoter located 5' of a non-lethal pertussis toxin gene and a non-lethal pertussis toxin gene located 3' of the tissue specific promoter. A non-lethal pertussis toxin gene of the 20 present invention includes the pertussis toxin genes described by Nicosia et al., Proc. Natl. Acad. Sci., 83:4631-4635 (1986); Locht et al., Science. 232:1258-1264 (1986) and Pizza et al., Proc. Natl. Acad. Sci., 85:7521-7525 (1988). The present invention also contemplates a segment of the pertussis toxin S1 gene that encodes a polypeptide that is an enzyme that can catalyze the ADP-ribosylation and inactivation of $G_g$ and $G_i$, the GTP-binding regulatory components that can stimulate protein kinase C and inhibit $G_s$ function. Other pertussis toxin genes or segments of genes that non-randomly hybridize to nucleotides 609 to 1313 of FIGS. 2A–2B or their complement are also contemplated by the present invention.

B. CELLS, TISSUES. AND ORGANISMS CONTAINING A NON-LETHAL MODULATOR GENE

1. Cells Containing A Non-Lethal Modulator Gene

The present invention contemplates a cell containing a recombinant nucleic acid molecule of the present invention. The recombinant nucleic acid molecule contains a tissue specific promoter located 5' of a non-lethal modulator gene and a non-lethal modulator gene. The recombinant nucleic acid molecule can be operatively linked to a vector for amplification and/or expression. As used herein, the term "vector" refers to a nucleic acid molecule capable of transporting between different genetic environments another nucleic acid to which it has been operatively linked. One type of preferred vector is an episome, i.e., a nucleic acid capable of extra-chromosomal replication. Preferred vectors are those capable of autonomous replication and/expression of nucleic acids to which they are linked. Vectors capable of directing the expression of genes to which they are operatively linked are referred to herein as "expression vectors". The choice of vector to which a non-lethal modulator gene of the present invention is operatively linked depends directly, as is well known in the art, on the functional properties desired, e.g., replication or protein expression, and the host cell to be transformed, these being limitations inherent in the art of constructing recombinant DNA molecules. In preferred embodiments, the vector utilized includes a prokaryotic replicon i.e., a DNA sequence having the ability to direct autonomous replication and maintenance of the recombinant DNA molecule extra-chromosomally when introduced into a prokaryotic host cell, such as a bacterial host cell. Such replicons are well known in the art. In addition, preferred embodiments that include a prokaryotic replicon also include a gene whose expression confers a selective advantage, such as a drug resistance, to the bacterial host cell when introduced into those transformed cells. Typical bacterial drug resistance genes are those that confer resistance to ampicillin or tetracycline.

Those vectors that include a prokaryotic replicon also typically include convenient restriction sites for insertion of a recombinant DNA molecule of the present invention. Typical of such vector plasmids are pUC8, pUC9, pBR322, and pBR329 available from BioRad Laboratories, (Richmond, CA) and pPL, pK and K223 available from Pharmacia, (Piscataway, N.J.), and pBLUESCRIPT and pBS available from Stratagene,(La Jolla, Calif.). A vector of the present invention may also be a Lambda phage vector including those Lambda vectors described in *Molecular Cloning: A Laboratory Manual, Second Edition,* Maniatis et al., eds., Cold Spring Harbor, N.Y. (1989), and the Lambda ZAP vectors available from Stratagene, (La Jolla, Calif.).

Expression vectors compatible with eukaryotic cells, preferably those compatible with vertebrate cells or plant cells can be used. Eukaryotic cell expression vectors are well known in the art and are available from several commercial sources. Typically, such vectors provide convenient restriction sites for insertion of the desired recombinant DNA molecule. Typical of such vectors are pSVO and pKSV-10 (Pharmacia), and pPVV-1/PML2d (International Biotechnology, INc.), and pTDT1 (ATCC, No. 31255). Typical expression vectors capable of expressing a recombinant nucleic acid sequence in plant cells include vectors derived from the tumor-inducing (Ti) plasmid of *agrobacterium tumefaciens* described by Rogers et al., *Meth. in Enzymol.,* 153:253–277 (1987), and several other expression vector systems known to function in plants. See for example, Verma et al., *PCT Publication No. WO87/00551*: Cocking and Davey, *Science.* 236:1259–1262 (1987).

In preferred embodiments, the eukaryotic cell expression vectors used include a selection marker that is effective in a eukaryotic cell, preferably a drug resistance selection marker. A preferred drug resistance selection marker is a gene whose expression results in neomycin resistance, i.e., the neomycin phosphotransferase (neo) gene. See for example, Southern et al., *J. Mol. Appl. Genet.,* 1:327–341 (1982). In preferred embodiments where a recombinant nucleic acid molecule of the present invention is expressed in plant cells a preferred drug resistance marker is the gene whose expression results in kanamycin resistance, i.e., the chimeric gene containing nopaline synthetase promoter, Tn5 neomycin phosphotransferase II and nopaline synthetase 3' non-translated region described by Rogers et al., *Methods for Plant Molecular Biology,* A. Weissbach and H. Weissbach, eds., Academic Press, Inc., San Diego, Calif. (1988).

The use of retroviral expression vectors to express recombinant nucleic acid molecules of the present invention is also contemplated. As used herein, the term "retroviral expression vector" refers to a DNA molecule that includes a promoter sequence derived from the long terminal repeat "LTR" region of a retrovirus gene and which is encapsulated in the viral protein coat capable of introducing the DNA into cells and integrating it into the cell's genome. In preferred embodiments, the expression vector is typically a retroviral expression vector that is preferably replication-incompetent in eukaryotic cells. The construction and use of retroviral vectors has been described by Sorge et al., *Mol. Cell Biol.,* 5 4:1730–1737 (1984).

In another preferred embodiment the expression vector is a retroviral expression vector that is replication incompetent and which already carries a marker gene such as the beta galactosidase gene. This marker gene allows cells infected by the retroviral vector to be identified by detecting the presence of the marker gene. Typically the marker gene is placed in the retroviral vector so that the non-lethal modulator gene must be coexpressed with the marker gene.

Replication incompetent retroviral expression vectors can be used to infect eukaryotic cells or tissues such as neurons and cortical progenitor cells. The infection may occur in vivo or in vitro. Retroviral vectors carrying a beta galactosidase marker gene have been used to infect neurons by Luskin et al., *Neuron,* 1:635–647 (1988).

A marker gene is a gene that codes for a protein that can be detected when expressed in a particular cell or cell type.

2. Tissues Containing A Non-Lethal Modulator Gene

Also contemplated by the present invention are tissues containing a recombinant nucleic acid molecule of the present invention. Tissues containing a recombinant nucleic acid molecule of the present invention may be prepared by introducing a recombinant nucleic acid molecule into a tissue, such as bone marrow, brain and liver, using known transformation techniques. These transformation techniques include transfection and infection by retroviruses carrying either a marker gene or a drug resistance gene. See for example, *Current Protocols in Molecular Biology*, Ausubel et al., eds., John Wiley and Sons, New York (1987) and Friedmann, T., *Science*, 244:1275–1281 (1989). A tissue containing a recombinant nucleic acid molecule of the present invention may then be reintroduced into an animal using reconstitution techniques. See for example, Dick et al., *Cell.* 42:71 (1985).

A tissue containing a recombinant nucleic acid molecule of the present invention may also be prepared by introducing a recombinant DNA molecule of the present invention into the germ line of a mammal. After introduction into the germ line the recombinant DNA molecule is present in all the tissues of that mammal. See for example, Palmiter, et al., *Ann. Rev. Genet.*, 20:465–499 (1986).

Isolation of tissues from an animal whose tissues contain the recombinant nucleic acid molecule is accomplished using standard techniques. For example, the liver, lungs, spleen, or bone marrow can be removed using standard surgical techniques.

A tissue containing a recombinant DNA molecule of the present invention may also be produced by directly introducing a vector containing the recombinant DNA molecule into the animal. Direct vector delivery in vivo may be accomplished by transducing the desired cells and tissues with viral vectors or other physical gene transfer vehicles in vivo. Other physical agents including naked plasmids, cloned genes encapsulated in targetable liposomes or in erythrocyte ghosts have been use to introduce genes, proteins, toxins and other agents directly into whole animals. See, for example, the liposome-mediated gene delivery in vivo and expression of preproinsulin genes in recipient rats described by Nikolau, et al., *Proc. Natl. Acad. Sci., U.S.A.*, 80:1068 (1983) and Soriano, et al., *Proc. Natl. Acad. Sci., U.S.A.*, 80:7128 (1983). Direct injection of naked calcium phosphate-precipitated plasmid into rat liver and rat spleen or a protein-coated plasmid into the portal vein has resulted in gene expression of the foreign gene in the rat livers. See for example, Kaneda, et al., *Science*, 243:375 (1989).

3. Animals Containing a Non-Lethal Modulator

The present invention also contemplates a mammal containing a recombinant nucleic acid molecule of the present invention. Mammals containing recombinant nucleic acid molecules of the present invention may be prepared using the standard transgenic technology described in Hogan et al., *Manipulating the Mouse Embryo: A Laboratory Manual*, Cold Spring Harbor, N.Y. (1987), Palmiter et al., *Ann. Rev. Genet.*, 20:465–499 (1986). Production of transgenic animals is also possible using the homologous recombination transgenic systems described by Capecchi, *Science*, 244:288–292 (1989).

One technique for transgenically altering a mammal is to microinject a recombinant nucleic acid molecule into the male pronucleus of the fertilized mammalian egg to cause 1 or more copies of the recombinant nucleic acid molecule to be retained in the cells of the developing mammal. The recombinant nucleic acid molecule of interest is isolated in a linear form with most of the sequences used for replication in bacteria removed. Linearization and removal of excess vector sequences results in a greater efficiency in production of transgenic mammals. See for example, Brinster, et al., *Proc. Natl. Acad. Sci., U.S.A.*, 82:4438–4442 (1985). Usually up to 40 percent of the mammals developing from the injected eggs contain at least 1 copy of the recombinant nucleic acid molecule in their tissues. These transgenic mammals usually transmit the gene through the germ line to the next generation. The progeny of the transgenically manipulated embryos may be tested for the presence of the construct by Southern blot analysis of a segment of tissue. Typically, a small part of the tail is used for this purpose. The stable integration of the recombinant nucleic acid molecule into the genome of transgenic embryos allows permanent transgenic mammal lines carrying the recombinant nucleic acid molecule to be established.

Alternative methods for producing a mammal containing a recombinant nucleic acid molecule of the present invention include infection of fertilized eggs, embryo-derived stem cells, totipotent embryonal carcinoma (Ec) cells, or early cleavage embryos with viral expression vectors containing the recombinant nucleic acid molecule See for example, Palmiter et al., *Ann. Rev. Genet.*, 20:465–499 (1986) and Capecchi, *Science*, 244:1288–1292 (1989).

C. METHODS OF GENETICALLY PROGRAMMING A CELL WITHIN AN ORGANISM WITH A NON-LETHAL MODULATOR GENE

The present invention also contemplates a method of genetically programming a cell within an organism by introducing a recombinant nucleic acid molecule of the present invention into the genome of a zygote to produce a genetically altered zygote or into the genome of individual somatic cells in the organism. The genetically altered zygote is then maintained under appropriate biological conditions for a time period equal to a gestation period or a substantial portion of a gestation period that is sufficient for the genetically altered zygote to develop into a transgenic organism containing at least 1 recombinant nucleic acid molecule of the present invention. The transgenic organism is then maintained for a time period sufficient for the non-lethal modulator gene present in the recombinant nucleic acid molecule to be expressed within a cell or cell type of the transgenic organism and thereby genetically program the cell within the organism.

The term "genetically programming" as used herein means to permanently alter the DNA, RNA, or protein content of a cell within an organism such as a mammal and thereby produce a biological effect. Typically, this genetic programming is accomplished by introducing a recombinant nucleic acid molecule of the present invention into the genome of the organism.

Any multicellular eukaryotic organism which undergoes sexual reproduction by the union of gamete cells may be genetically programmed using a nucleic acid molecule containing a non-lethal modulator gene. Examples of such multicellular eukaryotic organisms include amphibians, reptiles, birds, mammals, bony fishes, cartilaginous fishes, cyclostomes, arthropods, insects, mollusks, thallaphytes, embryophytes including gymnosperms and angiosperms. In preferred embodiments, the multicellular eukaryotic organism is a mammal, bird, fish, gymnosperm or an angiosperm.

A transgenic organism is an organism that has been transformed by the introduction of a recombinant nucleic acid molecule into its genome. Typically, the recombinant nucleic acid molecule will be present in all of the germ cells and somatic cells of the transgenic organism. Examples of transgenic organisms include transgenic mammals, transgenic fish, transgenic mice, transgenic rats and transgenic plants including monocots and dicots. See for example, Gasser et al., *Science*. 244:1293–1299 (1989); European Patent Application No. 0257472 filed Aug. 13, 1987 by De La Pena et al.; PCT Pub. No. WO88/02405 filed Oct. 1, 1987 by Trulson et al.; PCT Pub. No. WO87/00551 filed Jul. 16, 1986 by Verma, and PCT Pub. No. WO88/09374 filed May 20, 1988 by Topfer et al.

Methods for producing transgenic organisms containing a recombinant nucleic acid molecule of the present invention include standard transgenic technology; infection of the zygote or organism by viruses including retroviruses; infection of a tissue with viruses and then reintroducing the tissue into an animal; and introduction of a recombinant nucleic acid molecule into an embryonic stem cell of a mammal followed by appropriate manipulation of the embryonic stem cell to produce a transgenic animal. See for example, Wagner, et al., U.S. Pat. No. 4,873,191 (Oct. 10, 1989): Rogers, et al., *Meth. in Enzymol.*, 153:253–277 (1987); Verma et al., PCT Publication No. WO87/00551: Cocking et al., Science, 236:1259–1262 (1987); and Luskin et al., *Neuron* 1:635–647 (1988).

A cell within the organism that contains the recombinant nucleic acid molecule of the present invention is maintained for a time period sufficient for the non-lethal modulator gene present in the recombinant nucleic acid molecule to be expressed within that cell and thereby genetically program the cell of the organism.

Typically, the cell is maintained under biological growth conditions, appropriate for that organism for a sufficient time period. The biological growth conditions must allow the cell containing the recombinant nucleic acid molecule to express the non-lethal modulator gene present on the recombinant nucleic acid molecule. This time period is typically of a length to allow the non-lethal gene present in the recombinant nucleic acid molecule to be expressed. During expression the non-lethal modulator gene is first transcribed into RNA by RNA polymerase and then the RNA is translated into protein to produce the non-lethal modulator. The non-lethal modulator then modulates a complex biochemical pathway of the cell in which the chain is expressed but is not lethal to that cells.

Preferred embodiments of the present invention contemplate a method of altering a complex biochemical pathway within a cell of a transgenic mammal by producing a transgenic mammal having at least 1 cell containing and expressing a recombinant nucleic acid molecule of the present invention. The recombinant nucleic acid molecule containing transgenic mammal is maintained for a time period sufficient for the non-lethal modulator gene present in the recombinant nucleic acid molecule to be expressed in the cell and thereby altering a complex biochemical pathway within the cell of the transgenic mammal.

Transgenic mammals having at least 1 cell containing a recombinant nucleic acid molecule of the present invention can be produced using methods well known in the art. See for example, Wagner et al., U.S. Pat. No. 4,873,191 (Oct. 10, 1989); Hogan et al., *Manipulating the Mouse Embryo: A Laboratory Manual, Cold Springs Harbor, New York* (1987); Capecchi, *Science*, 244:288–292 (1989); and Luskin et al., *Neuron* 1:635–647 (1988).

In preferred embodiments the transgenic mammal of the present invention is produced by:
1) microinjecting a recombinant nucleic acid molecule into a fertilized mammalian egg to produce a genetically altered mammalian egg;
2) implanting the genetically altered mammalian egg into a host female mammal;
3) maintaining the host female mammal for a time period equal to a substantial portion of a gestation period of said mammal.
4) harvesting a transgenic mammal having at least one cell containing a recombinant nucleic acid molecule of claim 1 that has developed from the genetically altered mammalian egg.

A recombinant nucleic acid molecule of the present invention is provided, typically in linearized form, by linearizing the recombinant nucleic acid molecule with at least 1 restriction endonuclease. In addition, the recombinant nucleic acid molecule containing the tissue specific promoter and non-lethal modulator gene may be isolated from the vector sequences using 1 or more restriction endonucleases. Techniques for manipulating and linearizing recombinant nucleic acid molecules are well known and include the techniques described in *Molecular Cloning: A Laboratory Manual, Second Edition*. Maniatis et al., eds., Cold Spring Harbor, N.Y. (1989).

A fertilized mammalian egg may be obtained from a suitable female mammal by inducing superovulation with gonadotropins. Typically, pregnant mare's serum is used to mimic the follicle-stimulating hormone (FSH) in combination with human chorionic gonadotropin (hCG) to mimic luteinizing hormone (LH). The efficient induction of superovulation in mice depends as is well known on several variables including the age and weight of the females, the dose and timing of the gonadotropin administration, and the particular strain of mice used. In addition, the number of superovulated eggs that become fertilized depends on the reproductive performance of the stud males. See, for example, *Manipulating the Embryo: A Laboratory Manual*, Hogan et al., eds., Cold Spring Harbor, N.Y. (1986).

The linearized recombinant nucleic acid molecule may be microinjected into the mammalian egg to produce a genetically altered mammalian egg using well known techniques. Typically, the linearized nucleic acid molecule is microinjected directly into the pronuclei of the fertilized mouse eggs as has been described by Gordon et al, *Proc. Natl. Acad. Sci., U.S.A.* 77:7380–7384 (1980). This leads to the stable chromosomal integration of the recombinant nucleic acid molecule in approximately 10 to 40 percent of the surviving embryos. See for example, Brinster et al., *Proc. Natl. Acad. Sci., U.S.A.*, 82:4438–4442 (1985). In most cases, the integration appears to occur at the 1 cell stage, as a result the recombinant nucleic acid molecule is present in every cell of the transgenic animal, including all of the primordial germ cells. The number of copies of the foreign recombinant nucleic acid molecule that are retained in each cell can range from 1 to several hundred and does not appear to depend on the number of recombinant nucleic acid molecules injected into the egg.

An alternative method for introducing genes into the mouse germ line is the infection of embryos with virus vectors. The embryos can infected by either wild-type or recombinant viruses leading to the stable of integration of viral genomes into the host chromosomes. See, for example, Jaenisch et at., *Cell*, 4:519-529 (1981). One particularly useful class of viral vectors are virus vector derived from retro-viruses. Retroviral integration occurs through a precise mechanism, leading to the insertion of single copies of the virus on the host chromosome. The frequency of obtaining transgenic animals by retroviral infection of embryos can be as high as that obtained by microinjection of the recombinant nucleic acid molecule and appears to depend greatly on the titre of virus used. See, for example, van der Putten et al., *Proc. Natl. Acad. Sci., U.S.A.*, 82:6148-6152 (1985).

Another method of transferring new genetic information into the mouse embryo involves the introduction of the recombinant nucleic acid molecule into embryonic stem cells and then introducing the embryonic stem cells into the embryo. The embryonic stem cells can be derived from normal blastocysts and these cells have been shown to colonize the germ line regularly and the somatic tissues when introduced into the embryo. See, for example, Bradley et al., *Nature*, 309:255-256 (1984). Typically, the embryo-derived stem cells are transfected with the recombinant nucleic acid molecule and the embryo-derived stem cells further cultured for a time period sufficient to allow the recombinant nucleic acid molecule to integrate into the genome of the cell. In some situations this integration may occur by homologous recombination with a gene that is present in the genome of the embryo-derived stem cell. See, for example, Capecchi, *Science*, 244:1288-1292 (1989). The embryo stem cells that have incorporated the recombinant nucleic acid molecule into their genome may be selected and used to produce a purified genetically altered embryo derived stem cell population. See, for example, Mansour et al., *Nature*, 336:348 (1988). The embryo derived stem cell is then injected into the blastocoel cavity of a preimplantation mouse embryo and the blastocyst is surgically transferred to the uterus of a foster mother where development is allowed to progress to term. The resulting animal is chimeric in that it is composed from cells derived of both the donor embryo derived stem cells and the host blastocyst. Heterozygous siblings are interbred to produce animals that are homozygous for the recombinant nucleic acid molecule. See for example, Capecchi, *Science*, 244:1288-1292 (1989).

The genetically altered mammalian egg is implanted into host female mammals. Methods for implanting genetically altered mammalian eggs into host females are well known. See, for example, Hogan et al., *Manipulating the Mouse Embryo: A Laboratory Manual*, Cold Spring Harbor Laboratory, Cold Spring Harbor, New York (1986). Pseudopregnant recipient females may be produced by mating females in natural estrus with vasectomized or genetically sterile males. After mating with a sterile male, the female reproduction tract becomes receptive for transferred embryos even though her own unfertilized eggs degenerate. The genetically altered mammalian eggs are then transferred to the ampullae or the uterine horns of the pseudopregnant recipient. If the genetically altered mammalian egg is transferred into the ampullae it must be enclosed in a zona pellucida membrane. If it is transferred into the uterine horns the genetically altered mammalian egg does not require a zona pellucida membrane.

The host female mammals containing the implanted genetically altered mammalian eggs are maintained for a sufficient time period to give birth to a transgenic mammal having at least 1 cell containing a recombinant nucleic acid molecule of the present invention that has developed from the genetically altered mammalian egg. Typically this gestation period is between 19 to 20 days depending on the particular mouse strain. The breeding and care of mice is well known. See for example, *Manipulating the Mouse Embryo: A Laboratory Manual*, Hogan et al., eds., Cold Spring Harbor, New York, (1986).

In other preferred embodiments, the transgenic animal of the present invention is produced by infecting an animal vector containing a marker gene and a tissue specific promoter operatively linked to a non-lethal modulator gene to produce a genetically altered animal cell.

A marker gene is a gene that codes for a protein that can be detected when expressed in a particular cell or cell type. Typical marker genes include beta galactosidase, luciferase. Use of a beta galactosidase marker gene has been described by Luskin et al., *Neuron.* 1:635-647 (1988).

The marker gene may be under the control of a separate promoter. In other embodiments the marker gene is under the same promoter that controls expression of the non-lethal modulator gene such that the marker gene is expressed only if the non-lethal modulator gene is. Detection of marker gene expression indicates that the non-lethal modulator is also being expressed in that cell or cell type.

The infection of cells within an animal using a replication incompetent retroviral vector has been described by Luskin et al., *Neuron*, 1:635-647 (1988).

The genetically altered animal is maintained for a period sufficient for the non-lethal modulator and the marker genes to be expressed and thereby mark and alter a complex biochemical pathway within the animal.

Typically the genetically altered animal is maintained for at least 24 hours to allow the retrovirus vector to incorporate into the genome of the cells that it infects.

The expression of a marker gene can be detected enzymatically, chemically or immunologically. See for example Luskin et al., *Neuron.* 1:635-647 (1988).

D. SYSTEMS UTILIZING ANIMALS CONTAINING NON-LETHAL MODULATOR GENES

An animal expressing a non-lethal modulator gene in specific tissues or cells can be used to test a material, composition, or compound suspected of being therapeutic or a carcinogen. The animal is exposed to the particular material or compound and the effect on the animal determined as an indication of the therapeutic value or carcinogenicity of the compound or material. The specific effects determined depend upon the tissue specific promoter used to express the non-lethal modulator in the animals.

1. Animals Expressing A Non-Lethal Modulator Gene in Pituitary Growth Hormone-Releasing Cells Animals expressing a non-lethal modulator gene in the pituitary were produced by expressing a cholera toxin gene from a rat growth hormone promoter as described in Examples 1 and 2.

Therapeutic compositions suspected of having a useful activity in treating gigantism and acromegaly, may be tested using this method. The therapeutic composition is introduced into the animal by any suitable method including injection or ingestion.

The animal is then maintained for a predetermined time period that is sufficient to allow the composition to produce a physiological effect. Typically, this time period ranges from several minutes to several days depending on the particular physiological effect and the time the therapeutic composition requires to act on this physiological process.

The physiological process or parameter assayed depends upon the particular alteration produced by the non-lethal modulator and the known mode of action of the therapeutic composition. For example, a therapeutic composition useful in treating gigantism might be assayed by measuring body weight and/or body size.

A change in a physiologic parameter is determined by measuring that parameter before introduction of the therapeutic composition into the animal and comparing that measured value to a measured value determined in identical manner after introduction of the therapeutic composition into the animal.

The transgenic animals of this invention can also be used to test a material or compound suspected of being a carcinogen or to test for secondary oncogenic events by either introducing into the animal the suspected carcinogen or otherwise causing the secondary oncogenic event to occur in these animals. The animals that have had the suspected carcinogen introduced them are then analyzed to determine the presence of neoplastic growth and this is an indicator of the carcinogenicity of the substance the animals have been exposed to. Alternatively, animals in which a suspected secondary oncogenic event has been caused to occur may be analyzed for the development of neoplastic growth as an indicator of the ability of that secondary oncogenic event to produce neoplastic transformation. The level of expression of the non-lethal modulator in the transgenic animals may alter the sensitivity of transgenic mice to the effects of either the suspected carcinogen or a secondary oncogenic event. Therefore, selection of transgenic mice with varying transgene copy numbers will alter the sensitivity of the transgenic mice to the suspected carcinogen or the secondary oncogenic event. For example, if a higher level of non-lethal modulator creates a greater sensitivity to a particular carcinogen, transgenic mice with a higher transgenic copy number would be particularly useful as carcinogen detection system.

2. Animals Expressing A Non-Lethal Modulator Gene in Pituitary Prolactin

Animals expressing a non-lethal modulator gene in the pituitary prolactin producing cells were produced by expressing a cholera toxin gene from a prolactin releasing cell specific promoter such as the prolactin promoter described by Crenshaw et al., *Genes and Develop.*, 959–972 (1989). Animals expressing a non-lethal modulator in the pituitary can be produced by expressing a cholera toxin gene from the prolactin promoter described by Crenshaw et al., *Genes and Develop.*, 3:959–972 (1989).

Therapeutic compositions suspected of having a useful activity in treating polycystic ovary disease, amenorrhea in females, male sexual impotence or pituitary cancer may be tested using this method. The therapeutic composition is introduced into the animal by any suitable method including injection or ingestion.

The animal is then maintained for a predetermined time period that is sufficient to allow the composition to produce a physiological effect. Typically, this time period ranges from several minutes to several days depending on the particular physiological effect and the time the therapeutic composition requires to act on this physiological process.

The physiological process or parameter assayed depends upon the particular alteration produced by the non-lethal modulator and the known mode of action of the therapeutic composition. For example, a therapeutic composition useful in treating gigantism might be assayed by measuring body weight and/or body size.

A change in a physiologic parameter is determined by measuring that parameter before introduction of the therapeutic composition into the animal and comparing that measured value to a measured value determined in identical manner after introduction of the therapeutic composition into the animal.

The transgenic animals of this invention can also be used to test a material or compound suspected of being a carcinogen or to test for secondary oncogenic events by either introducing into the animal the suspected carcinogen or otherwise causing the secondary oncogenic event to occur in these animals. The animals that have had the suspected carcinogen introduced them are then analyzed to determine the presence of neoplastic growth and this is an indicator of the carcinogenicity of the substance the animals have been exposed to. Alternatively, animals in which a suspected secondary oncogenic event has been caused to occur may be analyzed for the development of neoplastic growth as an indicator of the ability of that secondary oncogenic event to produce neoplastic transformation. The level of expression of the non-lethal modulator in the transgenic animals may alter the sensitivity of transgenic mice to the effects of either the suspected carcinogen or a secondary oncogenic event. Therefore, selection of transgenic mice with varying transgene copy numbers will alter the sensitivity of the transgenic mice to the suspected carcinogen or the secondary oncogenic event. For example, if a higher level of non-lethal modulator creates a greater sensitivity to a particular carcinogen, transgenic mice with a higher transgenic copy number would be particularly useful as carcinogen detection system.

The use of compounds or compositions such as niacinamide to repress or enhance the modulator protein's activity within a transgenic animal in conjunction with a system to test for a carcinogen is also contemplated.

3. Animal Expressing a Non-Lethal Modulator in Pituitary Thyroid Releasing Cells Animals expressing a non-lethal modulator in the anterior lobe of the pituitary are produced using the proopiomelanocortin (POMC) peptide hormone promoter described by Tremblay et al., *Proc. Natl. Acad. Sci., U.S.A.*, 85:8890–8894 (1988). These animals would have high levels of serum adrenocorticotropin hormone (ACTH) caused by the hyperactivation of the corticotropes in the pituitary. These high levels of serum ACTH result in all of the symptoms of Cushing's Syndrome, including excess salt and water retention, potassium depletion, excess protein catabolism, osteoporosis, anti-inflammatory, and anti-allergic effects, muscle weakness, and high blood pressure.

Therapeutic compositions suspected of treating any of the symptoms of Cushing's syndrome may be tested using this method.

The physiologic parameter or process monitored in these animals would depend on the suspected mode of action of the therapeutic compound. For example, the change in serum sodium, serum potassium, bone calcium content, inflammation, immune system function, or blood pressure may be determined.

4. Animal Expressing a Non-Lethal Modulator in the Thyroid

Animals expressing a non-lethal modulator in the thyroid are prepared using the beta thyroid stimulating hormone promoter described by Tatsumi et al., *Nippon Risho.* 47:2213–2220 (1989). These animals would have high levels of serum thyroid stimulating hormone (TSH) caused by the hyperactivation of the cells that produce TSH. These high levels of serum TSH result in all of the symptoms of Grave's Disease (hyperthyroidism), including goiter, exophthalmos (protruding eyes), and high metabolic rate.

Therapeutic compositions suspected of treating any of the symptoms of Grave's disease may be tested using this method.

The physiologic parameter or process monitored in these animals would depend on the suspected mode of action of the therapeutic compound. For example, the change in thyroid size, metabolic rate, and iodine uptake may be determined.

5. Animals Expressing a Non-Lethal Modulator in the Pancreas

Animals expressing a non-lethal modulator in the β-cells of the pancreas are produced using the insulin promoter described by Edwards et al., *Cell,* 58:161 (1989). These animals would have high levels of serum insulin caused by the hyperactivation of the β-cells of the pancreas. These high levels of serum insulin result in hypoglycemia, hyperinsulinemia, type II diabetes and pancreatic cancer.

Therapeutic compositions suspected of treating any of the symptoms of diabetes may be tested using this method.

The physiologic parameter or process monitored in these animals would depend on the suspected mode of action of the therapeutic compound. For example, the change in serum, insulin or glucose level may be determined.

6. Animals Expressing a Non-Lethal Modulator in the Mammary Glands

Animals expressing a non-lethal modulator in the mammary glands are produced using the mouse mammary tumor virus promoter described by Muller et al., *Cell,* 54:105 (1988). These animals would have high levels of lactation caused by the hyperactivation of the cells of the mammary glands. These high levels of lactation should confer resistance to breast cancer similar to the breast feeding-induced resistance to breast cancer observed in humans.

Therapeutic compositions suspected of reducing resistance to breast cancer may be tested using this method.

The physiologic parameter or process monitored in the animals would depend on the suspected mode of action of the therapeutic compound. For example, the change in the number of spontaneous occurrences in breast cancer may be determined.

The transgenic animals of this invention can also be used to test a material or compound suspected of being a breast carcinogen or to test for secondary oncogenic events in breast cancer by either introducing into the animal the suspected breast carcinogen or otherwise causing the secondary oncogenic event to occur in these animals. The animals that have had the suspected breast carcinogen introduced into them are then assayed to determine the presence of neoplastic growth and this is an indication of the carcinogenicity of the substance the animals have been exposed to. Alternatively, animals in which a suspected secondary oncogenic event has been caused to occur may be assayed for the development of neoplastic growth as an indicator of the ability of that second oncogenic event to produce neoplastic transformation. The level of the non-lethal modulator expressed in the transgenic animals may alter the sensitivity of the mice expressing the mouse mammary tumor virus-cholera toxin fusion gene to the effects of either the suspected breast carcinogen or a secondary oncogenic event. Therefore, selection of transgenic mice with varying transgene copy numbers will alter the sensitivity of the transgenic mice to the suspected carcinogen or the secondary oncogenic event. For example, if a higher level of the non-lethal modulator creates a greater sensitivity or resistance to a particular breast carcinogen, transgenic mice with a higher transgene copy number would be particularly useful as a carcinogen detection system or as a model for cancer-resistance.

The use of compounds or compositions such as niacinamide to repress or enhance the modulator protein's activity within a transgenic animal in conjunction with a system to test for a carcinogen is also contemplated.

7. Animals Expressing A Non-Lethal Modulator In The Immune System

Animals expressing a non-lethal modulator in B and T cells using the immunoglobulin promoter described by Grosschedl et al., *Cell,* 38:647–658 (1984). These animals would have altered immune systems caused by the activation or inactivation of the B and T cells of the immune system. These alterations in the immune systems result in symptoms such as hyperimmunity or hypoimmunity including hyperallergic and hypoallergic reactions and autoimmunity.

Therapeutic compositions suspected of treating any of the symptoms of immune disease may be tested using this method.

The physiologic parameter or process monitored in these animals would depend on the suspected mode of action of the therapeutic compound. For example, the number and activation state of both B and T cells may be determined.

8. Animals Expressing A Non-Lethal Modulator In The Alpha-1 Antitrypsin Producing Cells Animals expressing a non-lethal modulator in the alpha-1 antitrypsin producing cells are produced using the albumin promoter described by Palmiter et al., *Ann. Rev. Genet.,* 20:465–498 (1986). These animals would have high levels of serum antitrypsin caused by the hyperactivation of the liver cells that produce alpha-1 antitrypsin. These high levels of serum antitrypsin would break down the elastase created in the lungs by cigarette smoke and confer resistance to emphysema.

Therapeutic compositions suspected of treating any of the symptoms of emphysema may be treated using this method.

The physiologic parameter or process monitored in these animals would depend on the suspected mode of action of the therapeutic compounds. For example, the rate of lung elastase breakdown may be determined.

9. Animals Expressing A Non-Lethal Modulator In The Adipose Cells

Animals expressing a non-lethal modulator in adipose cells are produced using an adipose cell specific promoter. These animals would have high levels of hormone sensitive lipase, causing lipolysis, or the breakdown or stored fat. This animal would have many of the same symptoms seen in anorexia nervosa and staryation.

Therapeutic compositions suspected of treating any of the symptoms of anorexia disease may be tested using this method.

The physiologic parameter or process monitored in these animals would depend on the suspected mode of action of the therapeutic compound. For example, the body weight could be determined.

10. Animals Expressing A Non-Lethal Modulator In The Lungs

Animals expressing a non-lethal modulator in the lungs are prepared using a lung cell specific promoter. These animals would have high levels of watery mucous in the lungs caused by hyperactivation of the cells of the lungs. These high levels of watery mucous result in all to the symptoms of *Bordetella pertussis* infection in humans and activation of the same calcium channels inhibited in cystic fibrosis.

Therapeutic compositions suspected of treating any of the symptoms of Pertussis infection may be treated using this method.

The physiologic parameter or process monitored in these animals would depend on the suspected mode of action of the therapeutic compound. For example, the quantity of mucous produced by the lungs may be determined.

11. Animals Expressing A Non-Lethal Modulator In The Liver

Animals expressing a non-lethal modulator in the liver are prepared using a liver cell specific promoter such as the promoter described in Palmiter et al., *Ann. Rev. Genet.*, 20:465–499 (1986). These animals would have high rates of glycolysis in the liver caused by the hyperactivation of the cells of the liver. These high levels of glycolysis result in all of the symptoms of glycosuria (high serum glucose levels), low serum cholesterol and high serum levels of very-low-density-lipoproteins (VLDL's).

Therapeutic compositions suspected of treating any of the symptoms of glycosuria may be tested using this method.

The physiologic parameter or process monitored in these animals would depend on the suspected mode of action of the therapeutic compound. For example, the level of serum glucose, cholesterol or VLDL's may be determined.

12. Animals Expressing A Non-Lethal Modulator In The Kidney

Animals expressing a non-lethal modulator in the kidney are prepared using a kidney specific promoter. These animals would have high rates of renin and aldosterone caused by the hyperactivation of the cells of the kidney. These high levels of serum renin and aldosterone result in all of the symptoms of Conn's Syndrome including high blood pressure, potassium depletion, kidney damage, polyuria (hypokalemic nephropathy) and muscle weakness.

Therapeutic compositions suspected of treating any of the symptoms of Conn's Syndrome may be tested using this method.

The physiologic parameter or process monitored in these animals would depend on the suspected mode of action of the therapeutic compound. For example, the level of serum potassium and urinary protein may be determined.

13. Animals Expressing A Non-Lethal Modulator In The Brain

Animals expressing a non-lethal modulator in the brain are prepared using a neuron or brain specific promoter such as either the olfactory marker protein promoter described by Danciger et al., *Proc. Natl. Acad. Sci., U.S.A.*, 86:8565–8569 (1989); the neuron-specific enolase promoter described by Forss-Petter et al., *J. Neurosci. Res.*, 16:141-151 (1986) or the L-7 promoter described by Sutcliffe, *Trends in Genetics.* 3:73–76 (1987). Hyperactivation of various neurons would result in ataxia, wakefulness, insomnia, suppression of circadian rythyms, mental retardation, memory deficits, retinal degeneration, Parkinson's disease, epilepsy, Guillain-Barre syndrome and other neurotransmitter disorders.

Therapeutic compositions suspected of treating any of the symptoms of the neuronal hyperactivation or neuronal hypoactivation may be tested using this method.

The physiologic parameter or process monitored in these animals would depend upon the suspected mode of action of the therapeutic compound. For example, the change in memory could be determined.

14. Animals Expressing A Non-Lethal Modulator In Natural Killer Cells

Animals expressing a non-lethal modulator in natural killer cells are prepared using a natural killer cell specific promoter. These animals would have altered levels of natural killer cell activity caused by the activation or inactivation of the natural killer cells. These altered levels of natural killer cell activity result in a change in resistance to cancer.

Therapeutic compositions suspected of changing natural killer cell activity, or may be tested using this method.

The physiologic parameter or process monitored in these animals would depend on the suspected mode of action of the therapeutic compound. For example, natural killer cell activity or resistance to spontaneous tumors may be determined.

15. Animals Expressing a Non-Lethal Modulator in Spermatids

Animals expressing a non-lethal modulator in spermatids are prepared using a protamine 1 promoter that has been previously described by Braun et al., *Genes Development.* 3:793–802 (1989). These animals would have alterations in spermatogenesis, behavior of the fertilized embryo, and epigenetic methylation caused by second messenger dependent alteration of spermatid development. The change in spermatid development results in changes in fertility and birth defects.

Therapeutic compositions suspected of altering spermatogenesis may be tested using this method.

The physiologic parameter or process monitored in these animals would depend on the suspected mode of action of the therapeutic composition. For example, total sperm count may be determined.

16. Animals Expressing a Non-Lethal Modulator in Erythrocytes

Animals expressing a non-lethal modulator in erythrocytes are prepared using an erythrocyte specific promoter such as the globin promoter described by Magram et al., *Mol. Cell Biol.*, 9:4581–4584 (1989). These animals would have altered erythrocyte differentiation caused by the hyperactivation of the erythrocytes. The inhibited erythrocyte differentiation results in anemia. Alternatively expression of a non-lethal modulator in erythrocytes may cause an increase in globin and spectrin synthesis in mature erythrocytes.

Therapeutic compositions suspected of altering erythrocyte activity may be tested using this method.

The physiologic parameter or process monitored in these animals would depend on the suspected mode of action of the therapeutic compound or composition. For example, the number of erythrocytes present in circulation may be determined.

17. Animals Expressing a Non-Lethal Modulator in the Skin

Animals expressing a non-lethal modulator in skin cells are prepared using the keratin promoter described by Vassar et al., *Proc. Natl. Acad. Sci., U.S.A.,* 86:1563–1577 (1989). These animals would have high levels of skin cell activity caused by the hyperactivation of the keratinocytes. This hyperactivation of skin cells results in hyperkeratinosis and hirsutisum.

Therapeutic composition suspected of altering skin cell activity may be tested using this method.

The physiologic parameter or process monitored in these animals would depend on the suspected mode of action of the therapeutic compound or composition. For example, variation in skin color, texture, or hair growth may be determined.

The transgenic animals expressing a non-lethal modulator in skin cells can be used to test a material or compound suspected of being a skin carcinogen such as UV-light or to test for secondary oncogenic events in skin cancer by either introducing into the animal the suspected skin carcinogen or otherwise causing the secondary oncogenic event to occur in these animals. The animals that have had the suspected skin carcinogen introduced into them are then assayed to determine the presence of neoplastic growth and this is an indication of the carcinogenicity of the substance the animals have been exposed to. Alternatively, animals in which a suspected secondary oncogenic event has been caused to occur may be assayed for the development of neoplastic growth an the indication of the ability of that secondary oncogenic event to produce neoplastic transformation. The level of the non-lethal modulator expressed in the transgenic animals may alter the sensitivity of the mice expressing the non-lethal modulator gene from the keratin promotor to the effects of either the suspected skin carcinogen or to a secondary oncogenic event. Therefore, selection of transgenic mice with varying transgene copy numbers will alter the sensitivity of the transgenic mice to the suspected carcinogen or secondary oncogenic event. For example, if a higher level of the non-lethal modulator creates a greater sensitivity to the particular skin carcinogen, transgenic mice with a higher transgene copy number would be particularly useful as a carcinogen detection system.

The use of compounds or compositions such as niacinamide to repress or enhance the modulator protein's activity within a transgenic animal in conjunction with a system to test for a carcinogen is also contemplated.

18. Animals Expressing a Non-Lethal Modulator in the Eye Lens

Animals expressing a non-lethal modulator in the eye lens are prepared using an eye-lens specific promoter such as the alpha-crystallin promoter described by Breitman et al., *Development,* 106:457–463 (1989). These animals would have high levels of eye lens cell activity caused by the hyperactivation of the eye lens cells. These high levels of eye lens cell activity may produce lens-hardening, presbyopia or glaucoma.

Therapeutic composition suspected of reducing eye lens cell activity may be tested using this method.

The physiologic parameter or process monitored in these animals would depend on the suspected mode of action of the therapeutic compound. For example, eye lens cell activity or eye lens flexibility may be determined.

19. Animals Expressing a Non-Lethal Modulator in Bone

Animals expressing a non-lethal modulator in bone cells are prepared using a bone specific promoter such as the osteonectin promoter described by McVey et al., *J. Biol. Chem.,* 263:1,111–11,116 (1988). These animals would have high levels of bone cell activity caused by the hyperactivation of the osteoclasts. These high levels of bone cell activity result in hypercalcification and resistance to osteoporosis.

Therapeutic composition suspected of reducing bone cell activity may be tested using this method.

The physiologic parameter or process monitored in these animals would depend on the suspected mode of action of the therapeutic composition. For example, bone cell activity or bone density may be determined.

20. Animals Expressing a Non-Lethal Modulator in the Prostate

Animals expressing a non-lethal modulator in prostate cells are prepared using prostate-specific promoter similar to the promoter described by Allison et al., *Mol. Cel. Biol.,* 9:2254–2257 (1989). These animals would have high levels of prostate cell activity caused by the hyperactivation of the prostate cells. These high levels of prostate cell activity result in greater sensitivity to prostate cancer.

Therapeutic composition suspected of reducing prostate cancer and prostate cell activity may be tested in this method.

The physiologic parameter or process monitored in these animals would depend the suspected mode of the therapeutic compound for example, prostate cell activity or resistance to prostate cancer may be determined.

The transgenic animals expressing the non-lethal modulator in the prostate may be used to test a composition suspected of being a prostate carcinogen or to test for secondary oncogenic events in prostate cancer by either introducing into the animal the suspected prostate carcinogen or otherwise causing the secondary oncogenic event to occur in these animals. The animals that have had the suspected prostate carcinogen introduced into them are then assayed to determine the presence of neoplastic growth and this is an indication of the carcinogenicity of the composition the animals have been exposed to. Alternatively, animals in which a suspected secondary oncogenic event has been caused to occur may be assayed for the development of neoplastic growth as an indicator of the ability of that secondary oncogenic event to produce neoplastic transformation. The level of the non-lethal modulator expressed in the transgenic animal may alter the sensitivity of the mice expressing the non-lethal modulator gene in the prostate to the effects of either the suspected prostate carcinogen or a secondary oncogenic event. Therefore, selection of transgenic mice with varying transgene copy numbers will alter the sensitivity of the transgenic mice to the suspected prostate carcinogen or the secondary oncogenic event. For example, if a higher level of the non-lethal modulator in the prostate creates a greater sensitivity to a particular prostate carcinogen, transgenic mice with a higher transgene copy number would be particularly useful in a carcinogen detection system.

The use of compounds or compositions such as niacinamide to repress or enhance the modulator protein's activity within a transgenic animal in conjunction with a system to test for a carcinogen is also contemplated.

E. METHODS AND SYSTEMS FOR ALTERING THE ACTIVITY OF THE NON-LETHAL MODULATOR GENE WITHIN A TRANSGENIC ANIMAL

A method for altering the function or activity of the non-lethal modulator gene within transgenic animal using a chemical composition is also contemplated. In preferred embodiments, the composition is injected or introduced in the transgenic animal's diet. The composition may either activate or inactivate the non-lethal modulator. Alternatively, the chemical composition may activate or inactivate the tissue specific promoter and thereby alter the activity of the non-lethal modulator.

In preferred embodiments, the composition is niacinamide that inactivates cholera or pertussis toxin as described in Gill et al., *Proc. Natl. Acad. Sci., U.S.A.,* 75:3050–3054 (1978). Niacinamide is a form of vitamin B3 that can be orally administered and has been shown to inactivate cholera toxin in vitro and has been given chronically to mice by injection at levels which approximate the concentrations that are inhibitory in vitro. See Gill and Merrin, *Proc. Natl. Acad. Sci., U.S.A.,* 75:3050–3054 (1978) and Yamada et al., *Diabetes.* 31:749–753 (1982).

In other preferred embodiments a method of changing the activity of a non-lethal modulator within the cells of a mammal by introducing a physiologically effective amount of a compound capable of altering the activity of the non-lethal modulator into a transgenic animal containing a tissue specific promoter operatively linked to a non-lethal modulator gene. The mammal is then maintained for a predetermined time period sufficient to allow the compound to alter the activity of the non-lethal modulator gene.

Typically, the compound is introduced by any suitable means including ingestion, injection or trans-dermal administration.

The compound is introduced in a physiologically effective amount that is capable of altering the activity of the non-lethal modulator. This amount must be sufficient to deliver a concentration of compound capable of altering the activity of the modulator to the cells containing the modulator. The compound may directly bind or otherwise physically alter the modulator and therefore change or alter its activity.

This invention also contemplates a method of determining the therapeutic effectiveness of a composition by: (1) treating an animal comprised of cells containing a vector having a tissue specific promoter operatively linked to a non-lethal modulator gene with a predetermined, physiologically effective amount of a composition. (2) the treated animal is then maintained for a predetermined period of time sufficient to allow the composition to produce a physiologic effect when the modulator gene is being expressed. (3) Any change in the physiologic condition of the maintained animal is determined thereby determining the therapeutic effectiveness of the composition.

An animal comprised of cells containing a nucleic acid molecule having a tissue specific promoter operatively linked to a non-lethal modulator gene is treated with a predetermined, physiologically effective amount of a composition. Such animals are prepared according to the method of this invention. See for example, Examples 1–4.

The animals may be treated with the composition by injection, ingestion or trans-dermal administration. Preferably, the composition is either provided in the animal's diet or injected.

The treated animal is maintained for a predetermined period of time sufficient to allow the composition to produce a physiological effect for a predetermined time period during which said non-lethal modulator gene is being expressed.

Preferably, the treated animal is maintained long enough for the composition to travel from the administration site to the cell or cells containing the now-lethal modulator and to bind to or otherwise produce an effect on the modulator resulting in a physiological effect. The composition may produce a physiologic effect by directly binding or effecting the non-lethal modulator or by altering the expression of the non-lethal modulator. The expression of the non-lethal modulator may be altered by increasing or decreasing the rate of transcription from the tissue specific promoter. The composition may act to induce or suppress expression of the non-lethal promoter from the tissue specific promoter.

Any change in the physiologic condition of the maintained animal is determined thereby determining the therapeutic effectiveness of the composition. The physiologic condition of an animal is easily monitored and includes determining rate of weight gain, body size and the like. Compositions that alter the physiologic condition as compared to control animals may be useful in treating disease.

A composition is therapeutically effective if it alters the activity of the non-lethal modulator in a cell of a transgenic animal expressing the non-lethal modulator. The composition may alter the activity of the non-lethal modulator by changing the level of expression of the non-lethal modulator of by changing the biochemical activity of the non-lethal modulator.

EXAMPLES

The following EXAMPLES illustrate, but do not limit the present invention.

1. CONSTRUCTION OF THE NON-LETHAL MODULATOR GENE EXPRESSION VECTOR

A 600 base pair nucleic acid segment encoding the mature and enzymatically active A1 subunit of cholera toxin, a non-lethal modulator gene, was placed immediately 3' of the tissue specific promoter of the rat growth hormone gene to produce a tailored fusion gene encoding cholera toxin. To produce this gene, the 600 base pair region encoding the mature and enzymatically active A1 subunit of cholera toxin was amplified from the cloned ctx operon *Vibrio Cholerae* holotoxin using the polymerase chain reaction. The cloned for the *Vibrio Cholera* holotoxin has been completely sequenced and previously described by Mekalanos et al., *Nature*, 306:551-557 (1983) and is present in clone PRT41. The A1 subunit of cholera toxin is encoded by nucleotides 570 to 1151 of FIG. 1.

Polymerase chain reaction (PCR) primers were designed to remove sequences encoding the signal peptide for bacterial secretion, and the A2 subunit which is normally cleaved off after cell penetration, and the B subunit responsible for cell penetration. The PCR primers in Table II were synthesized using an automated oligonucleotide synthesizer. The PCR primers amplified nucleotides 570 to 1151 and added a consensus eukaryotic translation initiation site (CCACCATGG) and termination sites as described by Kozak, M, *Nucliec Acids Research.* 12:857-852 (1984). The PCR primers also added a termination codon (TAG) to the amplified A1 coding region as well as flanking Bam HI restriction endonuclease sites (GGATCC).

The PCR amplification was carried out by admixing in a 50 microliter reaction 100 nanograms (ng) of the cloned ctx operon of the *Vibrio Cholera* holotoxin DNA (Eco RI-linearized PRT41 template DNA) to a solution containing in 50 mM KCl, 10 mM Tris-HCl at pH 8.4, 1.5 mM MgCl$_2$, 250 pmole of primers CT-5' and CT-3' shown in Table II, 200 uM each of dATP, dCTP, dTTP, dGTP, 200 ug/ml of gelatin and 2 units of Taq polymerase (Cetus Corp., Emeryville, Calif.). The samples were overlaid with approximately 50 ul of mineral oil to prevent evaporation and subjected to 30 cycles of amplification according to the manufacturers instructions. In each amplification cycle the solution was heated to 92 C. over a 30 second time period to denature the DNA, cooled to 50 C. over two minutes to allow the primers to anneal with the *Vibrio Cholera* DNA, and maintained at 72 C. for 2 minutes to produce a complementary DNA (cDNA) strand from the *Vibrio Cholera* DNA. The resulting amplified DNA segment containing the A1 subunit of cholera toxin is flanked by Bam HI restriction endonuclease sites that allow the fragment to be easily inserted into a vector containing the tissue specific promoter.

The PCR reaction was tested for appropriate amplification by ethidium bromide staining and examination of 1/10th of the reaction, run on a 1% agarose electrophoresis gel. A band of the expected size (~600 bp) was seen, confirming appropriate amplification. The remainder of the PCR product was phenol-chloroform-isoamyl alcohol (64:32:4) extracted twice and ethanol precipitated to remove residual Taq polymerase activity and free nucleotides. 2 µg of the PCR product was then 5-fold over-digested with BamHI, the BamHI was inactivated by heating at 68° C. and then freezing, and then 20 ng of the BamHI-cut PCR product was ligated to 20 ng of the BamHI-cut and phosphatased rGH-hGH vector DNA.

TABLE II

| Polymerase Chain Reaction Primers | |
|---|---|
| CT-5': 5'GCGGATCCACCATGGGTAATGATGATAAGTTATAT | 3' |
| CT-3': 5'GCGGATCCTACGATGATCTTGGAGCATTCC | 3' |

The amplified DNA segment containing the A1 subunit of cholera toxin flanked by Bam HI restriction endonuclease sites was inserted into the unique Bam HI restriction endonuclease site within the 5' untranslated region of the rGH-hGH fusion gene previously described by Behringer et al., *Genes and Development,* 2:453-461 (1988). It consists of a 310 bp KpnI-XhoI fragment containing the rat growth hormone (rGH) promoter and transcription start site previously described by Braun et al., *Proc. Natl. Acad. Sci., U.S.A.,* 78:4867-4871 (1981), fused to a 2150 bp XhoI-EcoRI fragment containing the 5' untranslated region (containing a unique BamHI site) and remaining gene and 3' intergenic sequences for human growth hormone (hGH) previously described by Seeburg, DNA, 1:239-249 (1982), cloned into a pUC plasmid vector. It was prepared for insertion of the BamHI CT cassette by 6-fold over-digestion with BamHI, plus 0.0125 units/µg/hr calf intestinal alkaline phosphatase to prevent circularization during the ligation step. The Bam HI digested rGH-hGH plasmid was purified by extraction with phenol followed by ethanol precipitation. Twenty nanograms (ng) of the PCR amplified DNA segment was then ligated directly to 20 ng of Bam HI digested rGH-hGH plasmid using the ligation procedures described in *Molecular Cloning: A Laboratory Manual.* Maniatis et al., eds., Cold Spring Harbor, N.Y. (1982). Briefly, ligation was performed overnight at 15° C., in a 10 µl volume containing 1 weiss unit T4 DNA ligase (BRL), 50 mM Tris 7.5, 10 mM MgCl$_2$, 10 mM DTT, and 1 mM rATP.

A fifth (2 µl) of the ligation was diluted to 20 µl with TE buffer, and 100 µl of CaCl$_2$-treated transformation-competent cells (MC1061 strain) were added. After a 30 minute incubation on ice to allow ligated plasmid attachment to cells, the cells were incubated at 42° C. for 90 seconds to allow DNA entry into the cells, then 1 ml of 37° C. 2×LB broth was added and the cells placed at 37° C. for 40 minutes. 300 µl of the cells were then spread on LB-ampicillin agar plates. Ampicillin resistant colonies appeared on the plates after 12 hrs of 37° C. incubation. These colonies were screened for the presence of the putative recombinant plasmid by first hybridizing a colony lift of the plate with radiolabeled probe prepared from nick-translation of the PCR product to identify clones that carried the PCR-cassette insert, and then by restriction digesting plasmid miniprep DNA prepared from positive clones. First the DNA samples were cut with BamHI and analyzed by 1% agarose gel electrophoresis to confirm they contained the ~600 bp BamHI PCR-cassette. Then the DNA samples were double-digested with KpnI and XbaI, which generate restriction fragments of different size depending upon the orientation of the inserted BamHI PCR- cassette. By this means several clones of the recombinant plasmid with a correctly oriented insert were identified. Their PCR CT cassettes were sequenced by the dideoxy-method[7] using synthetic primers designed to sequence into the BamHI cloning site (5'-GAAAGGCAGGAGCCTTGGGG-3' and 5'-TGTCCACAGGACCCTGAGTG-3'), and were confirmed to have been PCR amplified and cloned without errors. One of these identical clones was chosen for embryo microinjection and designated rGH-CT.

A large scale plasmid preparation of the rGH-CT clone was prepared and the DNA isolated and purified by density gradient centrifugation in cesium chloride. The 3 kb rGH-CT fusion gene fragment was separated from pUC vector sequences by KonI-EcoRI digestion and 1% agarose gel electrophoresis. The KpnI-EcoRI gene fragment was cut out of the gel and purified from the 30 agarose by the NaI-glass powder purification method described by Vogelstein et al., *Proc. Natl. Acad. Sci., U.S.A.*, 76:615-619 (1979). The gene fragment was diluted to 1 ng/μl concentration centrifuged at 10,000 xg to remove residual sediment, and the resulting supernatant used for mouse embryo microinjections. The resulting cholera toxin expression vector contains a tissue specific rat growth hormone promoter located immediately 5' of the cholera toxin nucleic acid segment as shown in FIG. 3. The cholera toxin nucleic acid segment is located 5' of and controls the expression of the exons, introns, and polyadenylation site of the gene for human growth hormone. The tissue specific rat growth hormone promoter has been previously used in transgenic mice to specifically express human growth hormone and diphtheria toxin in pituitary somatotropes by Behringer et al., *Genes and Development*, 2:453-461 (1988) and Palmiter et al., *Cell.* 50:435-443 (1987). The cholera toxin expression vector retains in its 3' untranslated region that contains the nucleic acid segment of the human growth hormone gene for correct messenger RNA (mRNA) splicing and 3' end cleavage and polyadenylation. The accuracy of the above construction steps was confirmed by DNA sequencing using the Sanger dideoxy described by Sanger et al., *Proc. Natl. Sci. U.S.A.*, 74:5463-5467 (1977).

2. PRODUCTION OF TRANSGENIC MICE EXPRESSING THE TISSUE SPECIFIC CHOLERA TOXIN CONSTRUCT

Transgenic mice expressing the rGH-CT fusion gene were produced using the standard transgenic technology described in *Manipulating the Mouse Embryo: A Laboratory Manual*, Hogan et al., eds., Cold Spring Harbor, N.Y. (1986). The rGH-CT gene fragment was introduced into the mouse germ line in the following manner: male and female F1 C57BL/6×Balb/c hybrids were mated, and recently fertilized F2 hybrid eggs were removed from the females. The male pronucleus of 200 of these zygotes was injected with 2 pl containing ~700 molecules of the 3 kb rGH-CT gene fragment, and the zygotes were then transferred in equivalent batches into the oviducts of 23 pseudopregnant female mice prepared using the methods described by Brinster et al., *Cell*, 27:223-231 (1981). This procedure produced 68 transgenic animals from the microinjected eggs.

To determine which of the 68 mice contained transgenic DNA, genomic DNA was obtained from tail tissue removed from each mouse at 4 weeks of age: 1.5 to 2 cm of tail was clipped off, frozen at −70° C., and chopped into 6-8 sections which were added to 700 μl of 50 mM Tris 8.0, 10 mM EDTA, 100 mM NaCl, 1% SDS, and 20 μl of 20 mg/ml Proteinase K in an eppendorf tube. The SDS-Proteinase K treatment continued overnight to solubilize proteins, and then the samples were extracted once each with phenol 8.0, phenol chloroform-isoamyl alcohol 8.0 (64:32:4) and chloroform-isoamyl alcohol (24:1). Then the genomic DNA in the samples was ethanol precipitated by addition of 2 volumes of cold absolute ethanol followed by inverting the tube several times, and the DNA was removed by suction using a pipetteman tip, followed by dipping in 80% ethanol to rinse, and then air drying for 30 minutes or longer. The genomic DNA was then resuspended in 200 μl of 10 mM Tris 8.0, 0.1 mM EDTA, and 10 mM NaCl by gentle rocking on a nutator at 4 C. overnight. This procedure yielded 70-100 μg of genomic DNA per 1.5-2 cm tail piece. Equivalent amounts of genomic DNA from each animal were then loaded onto a nitrocellulose slot blot apparatus and the blotted DNA samples were hybridized with a radiolabeled probe prepared by nick translation of the PCR amplified CT DNA. All subsequent offspring of the positive transgenic founders among the original 68 mice were also analyzed by this method. This hybridization revealed that 13 of transgenic mice carried the transgene.

The number of transgenes present in each of the transgenic mice was determined by Southern blotting using the procedures first described by Southern, *J. Molec. Biol.*, 98:503-515 (1975). Briefly, the isolated nucleic acid was digested with Eco RI or Xba I restriction endonuclease then fractionated by size in an agarose gel. The size separated DNA was then transferred to a sheet of nitrocellulose and hybridized with a radiolabeled DNA probe prepared from the cholera toxin gene. Five transgenic mice had an apparent transgene copy number of less than or equal to one based on this Southern blot hybridization while nine had an apparent transgene copy number of greater than or equal to two. Of the original 13 transgenic mice, 9 had markedly higher serum growth hormone levels than nontransgenic littermates and 8 of these 9 had greater body weights. (Table I).

Seven of the nine transgenic mice with an apparent transgene copy number of greater than 2 and one transgenic mouse with an apparent copy number of less than or equal to 1 were bred to non-transgenic mates. Ninety seven $F_1$ generation mice were obtained and of those 97, 47 were transgenic. Southern blotting of DNA from these transgenic lines identified 10 transgenic loci of which 8 showed approximately 50 percent inheritance (Table I).

TABLE I

| GH levels and growth of rGH-CT transgenic mice. | | | |
|---|---|---|---|
| Mouse | Sex | Transgenic (+) | serum MGH (ng ml$^{-1}$) | growth (ratio) |
| $F_01$ | F | + | 848 | 1.43 |
| $F_13$ | M |   | 44 |   |
| $F_14$ | M | + | 580 | 1.33 |
| $F_15$ | M | + | 1430 | 1.22 |
| $F_16$ | M | . | 67 |   |
| $F_12$ | F | + | 617 | ND |

TABLE I-continued

GH levels and growth of rGH-CT transgenic mice.

| Mouse | Sex | Transgenic (+) | serum MGH (ng ml$^{-1}$) | growth (ratio) |
|---|---|---|---|---|
| $F_1 7$ | F | + | 1090 | ND |
| $F_0 8$ | F | + | 484 | 1.22 |
| $F_1 8$ | M | + | 545 | 1.53 |
| $F_1 9$ | M | + | 408 | 1.31 |
| $F_1 10$ | M | + | 226 | 1.17 |
| $F_1 11$ | M | | 15 | |
| $F_1 12$ | M | + | 868 | 1.53 |
| $F_1 14$ | F | | 8 | |
| $F_1 15$ | F | + | 505 | 1.55 |
| $F_0 15$ | M | + | 639 | 1.29 |
| $F_1 16$ | M | + | 413 | 1.47 |
| $F_1 24$ | M | | 121 | |
| $F_1 17$ | F | + | 143 | 1.16 |
| $F_1 19$ | F | | 12 | |
| $F_1 21$ | F | + | 361 | 1.55 |
| $F_1 22$ | F | + | 421 | 1.24 |
| $F_1 23$ | F | | 17 | |
| $F_0 19$ | M | + | 432 | 1.34 |
| $F_1 42$ | F | | 43 | |
| $F_1 43$ | F | + | 691 | 1.16 |
| $F_1 45$ | F | | 13 | |
| $F_0 44$ | F | + | 371 | 1.22 |
| $F_1 46$ | M | | <7 | |
| $F_1 47$ | M | | <7 | |
| $F_1 48$ | M | + | 932 | 1.47 |
| $F_1 49$ | F | | <7 | |
| $F_1 52$ | F | + | 538 | 1.34 |
| $F_1 54$ | F | + | 415 | 1.19 |
| $F_0 52$ | M | + | 339 | 0.96 |
| $F_1 55$ | M | + | 108 | 1.27 |
| $F_1 56$ | M | | 16 | |
| $F_1 57$ | M | + | 336 | 1.08 |
| $F_1 58$ | F | + | 87 | 1.12 |
| $F_1 59$ | F | + | 78 | 1.28 |
| $F_1 60$ | F | | <7 | |
| $F_1 61$ | F | + | 505 | 1.42 |
| $F_1 62$ | F | + | 250 | 1.58 |
| $F_0 62$ | M | + | 753 | 1.07 |
| $F_1 64$ | M | + | 736 | 1.07 |
| $F_1 66$ | M | | 16 | |
| $F_1 73$ | M | | <7 | |
| $F_1 74$ | M | | <7 | |
| $F_1 75$ | M | + | 292 | 1.17 |
| $F_1 76$ | M | + | 155 | 1.39 |
| $F_1 67$ | F | | 42 | |
| $F_1 68$ | F | + | 279 | 1.12 |
| $F_1 69$ | F | + | 387 | 1.27 |
| $F_1 70$ | F | + | 456 | 1.34 |
| $F_1 72$ | F | | 76 | |
| $F_0 65$ | F | + | 466 | 1.22 |
| $F_1 79$ | M | + | 1980 | ND |
| $F_1 80$ | M | + | 2940 | ND |
| $F_1 81$ | M | + | 292 | ND |
| $F_1 83$ | F | + | 80 | 1.08 |
| $F_1 84$ | F | | <7 | |
| $F_1 85$ | F | + | 369 | 1.27 |
| $F_1 86$ | F | | 9 | |
| $F_1 87$ | F | + | 26 | 1.18 |
| $F_0 33$ | M | + | 44 | 0.97 |
| $F_0 35$ | F | + | 10 | 0.91 |
| $F_0 36$ | F | + | 462 | 1.12 |
| $F_0 37$ | F | + | 7 | 0.98 |
| $F_0 43$ | F | + | 56 | 1.11 |

3. ANALYSIS OF TRANSGENIC MICE EXPRESSING THE rGH-CT FUSION GENE

The original founder, F transgenic and non-transgenic littermate mice were weighed and endogenous serum growth hormone (mGH) determined coxuercially by specific double antibody radioimmunoassay (Mazleton Biotechnologies Company, Vienna Va.). The average mGH level of 35 $F_1$ transgenic mice (558 ng/ml) was >21 fold higher (P<0.001) than that of 21 $F_1$ control littermates (<26 ng/ml, Table I). The highest individual transgenic mouse serum mGH level was 2940 ng/ml (Table I). The weights and mGH serum values are similar to those exhibited by transgenic mice that express high serum levels of growth hormone releasing factor from the metallothionein promoter as has been previously described by Hammer et al., *Nature*, 315:413–416 (1985). No human growth hormone production was detected in any of the transgenic lines assayed confirming the assumption that insertion of the cholera toxin gene into the 5' untranslated region of the rGH-hGH prevents expression of the downstream human growth hormone gene.

Expression of the rGH-CT fusion gene in the transgenic mice elevated the level of intracellular cyclic AMP which was sufficient to cause all the responses normally seen to growth hormone releasing factor including the stimulation of growth hormone transcription, the secretion of growth hormone, and somatotrope proliferation. The transgene elevated cyclic AMP to supraphysiological concentrations that were sufficient cause permanently elevated growth hormone production and pituitary hyperplasia which mimics the effects of excess serum growth hormone releasing factor in mice and humans.

The serum prolactin levels of the transgenic mice were measured using the assay developed by Hazelton Biotechnologies Company (Vienna, Va.). The serum prolactin levels were not elevated in the transgenic mice relative to controls.

The serum thyroid stimulating hormone levels in the transgenic mice were measured using the assay developed by Hazelton Biotechnologies Company (Vienna, Va.). The level of serum thyroid stimulating hormone present in the transgenic mice was not elevated relative to controls. The lack of elevation of prolactin and thyroid stimulating hormone levels in the serum indicates that the transgene's action is appropriately specific to growth—hormone releasing somatotropic cells of the pituitary.

The high serum growth hormone levels caused by the stimulation of the $G_s$ protein is chronic, evidenced by measuring the growth hormone level in mice of various ages. The growth hormone level in 5.5 to 7.5 month old $F_1$ mice and from 10 month old founder mice indicated that the stimulation of serum growth hormone production continues long into adulthood rather than halting after adolescence.

Figure 4A:

Whole pituitaries were isolated from the transgenic mice and non-transgenic littermates, weighed and photographed (FIGS. 4A-4L). The transgenic pituitaries were markedly larger than control pituitaries (FIG. 4A). The anterior lobes of the pituitaries were clearly ballooned. Pituitaries from 3 mice with highly elevated growth hormone levels (848 to 2940 ng/ml) weighed 7 mg, 9 mg and 9.3 mg, respectively compared to the control pituitaries weight of 1.5 mg. The pituitaries from 8 transgenic mice with moderately elevated serum growth hormone levels ranging from 336 to 736 ng/ml weighed an average of 4.5 mg (standard deviation=0.8 mg) compared to the average of 8 control mice of 1.9 mg (standard deviation=0.4 mg). The transgenic pituitary sizes were proportionally increased from approximately 2 fold to 6 fold. In transgenic mice expressing growth hormone from the metallothionein promoter as previously described by Palmiter et al., *Nature*, 300:611–615 (1982) the pituitary size is actually decreased relative to control mice as described by Stefaneanu et al., *Endocrinology* 126:608–615 (1990).

This effect is presumably due to the action of somatostatin on the pituitaries as has been described by Jakobs et al., *Nature*, 303:177–178 (1983). The transgenic mice expressing the cholera toxin appear to be insensitive to the action of somatostatin because of their constitutive activation of the $G_s$ protein.

Figure 4B:
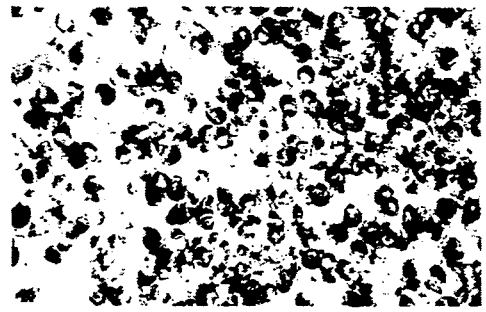
Figure 4C:
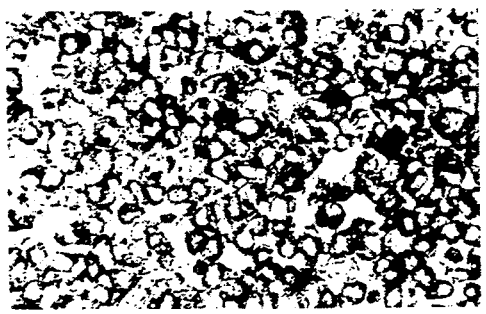
Figure 4D:
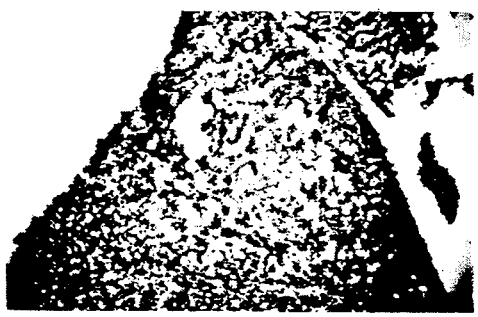
Figure 4E:
Figure 4F:
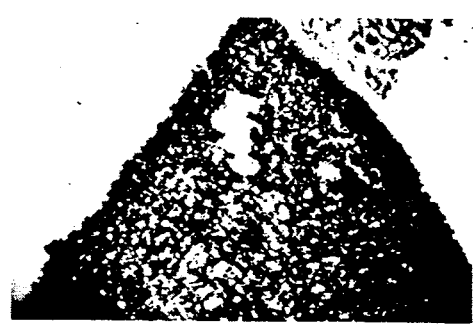
Figure 4G:
Figure 4H:
Figure 4I:
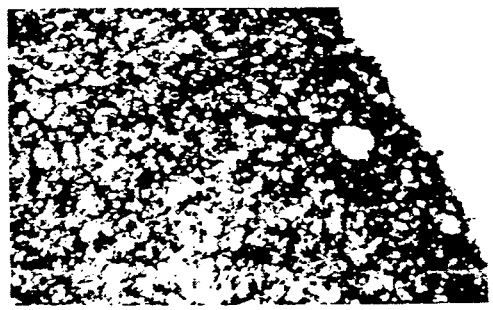
Figure 4J:
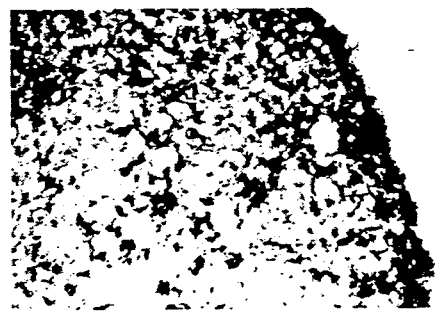
Figure 4K:
Figure 4L:
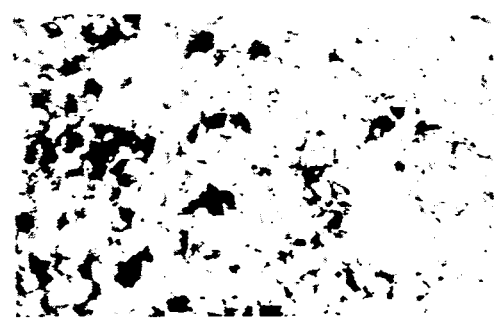

The hyperplasia of the rGH-CT transgenic pituitaries could be due to proliferation of growth hormone releasing cells, i.e., the somatotropes, or the proliferation of both somatotropes and mammosomatotropes, which are growth hormone releasing cells in the process of converting to prolactin releasing cells, and thus transiently releasing both growth hormone and prolactin as has been previously described by Hoeffler, et al., *Endocrinology*. 117:189–185 (1985). This pathway produces most of the prolactin releasing cells in normal mice except for a small population of cells that may originate directly from the pituitary stem cells as described by Behringer, et al., *Genes and Development*, 2:453–461 (1988). To determine which particular cell type was responsible for the hyperplasia of the rGH-CT transgenic pituitaries, the pituitaries were stained using histochemical stains and specific antisera for growth hormone, cholera toxin, prolactin, and thyroid stimulating hormone. Pituitaries isolated from transgenic male mice expressing the rGH-CT fusion gene were isolated and the number of growth hormone reactive pituitary cells determined (FIGS. 4B and 4C). Approximately 50% of normal pituitary cells were growth hormone reactive and approximately 85% to 90% of the transgenic pituitary cells were reactive with growth hormone. Cells weakly staining for cholera toxin c-localized with the growth hormone positive cells (FIGS. 4D-G). There was no increase number of prolactin reactive cells or thyroid stimulating hormone reactive cells and an apparent decrease in the number of prolactin positive cells was detected in the male transgenic mice (FIGS. 2H-L). This reduction in prolactin positive cells in the transgenic mouse expressing the rGH-CT fusion gene is in direct contrast with the amplified population of cells that are positive for both growth hormone and prolactin that are detected in transgenic mice expressing a growth hormone releasing factor gene from a metallothionein promoter as described by Stefaneanu et al., *Endocrinology*, 125:2710–2718 (1989).

An important difference between the transgenic mice expressing the rGH-CT fusion gene and the transgenic mice expressing the growth hormone releasing factor from a metallothionein promoter (MT-GRF) is that somatotrope $G_s$-activity in the MT-GRF mice should be inhibitable, at least partly, by somatostatin-induced $G_i$-activity as has been described by Hoeffler et al., *Endocrinology*, 117:189–185 (1985). The transgenic mice expressing the rGH-CT fusion gene should have a $G_s$-activity that is not inhibitable. This constitutive $G_s$-activity would not be inhibited by the higher somatostatin levels induced by the excess serum growth hormone levels and thus if somatostatin triggers the mammosomototrope transition, it should not be triggered in the transgenic mice expressing the rGH-CT fusion gene. A second important difference between these two types of transgenic mice is that the rGH-CT mice do not have aberrantly high serum GRF levels. If the higher serum GRF is causing the mammosomototrope transition, then it must do so by a novel means other than its known function of elevating cAMP levels. This is because the rGH-CT mice have elevated cAMP levels, but do not undergo the conversion. In the rGH-CT transgenic male mice the small population of prolactin positive cells that remain may be those prolactin cells that are thought not to arise from growth hormone positive precursor cells as has been described by Behringer et al., *Genes and Development*, 2:453–461 (1988). The female transgenic mice expressing the rGH-CT fusion gene have greater numbers of prolactin positive cells than the males expressing this gene perhaps due to a sex-specific clonal expansion of this small population of cells or an ability in these female mice to stimulate the mammosomatotrope transition via another regulatory pathway.

4. ASSAY SYSTEM FOR CARCINOGENICITY AND Second CARCINOGENIC EVENTS

The pituitaries from the transgenic mice expressing rGH-CT fusion gene were examined at the gross anatomical level and in histological sections for the presence of neoplastic cells. 1 of the 24 transgenic pituitaries isolated from these mice showed tentative evidence of a growth hormone releasing tumor that exhibited cell homogeneity, mitotic figures, increased vascularization and blood cells, and an evident positive lesion upon gross morphological examination. Also, the tumor was focal rather than widespread within the pituitary tissue. Previously, elevated somatotrope cAMP has been correlated with the presence of slowly evolving and late-onset tumors in humans by Vallar et al., *Nature*, 330:566–568 (1987); Asa et al., *J. Clin. Endocr. Metab*, 58:796–803 (1984); and Landis et al., *Nature*, 340:692–696 (1989). Our data showing infrequent, late-onset, and focal tumors suggest that the high cAMP levels present in the transgenic mice expressing the rGH-CT fusion gene only predisposes the cells for neoplasia rather than being sufficient by itself to trigger the development of tumors. Therefore, these transgenic mice are useful to detect second oncogenic events that may be required before neoplastic transformation can begin.

The transgenic animals of this invention are to be used to test a material suspected of being a carcinogen or to test for second oncogenic events by either exposing the animal to the suspected carcinogen or otherwise causing the second oncogenic event to occur in these animals. The animals that have been exposed to the suspected carcinogen are then analyzed to determine the presence of neoplastic growth and this is an indicator of the carcinogenicity of the substance the animals have been exposed to. Alternatively, animals in which a suspected second oncogenic event has been caused are analyzed for the development of neoplastic growth as an indicator of the ability of that second oncogenic event to produce neoplastic transformation.

The level of cyclic cAMP induced in the transgenic animals may alter the sensitivity of transgenic mice expressing the rGH-CT fusion gene to the effects of either the suspected carcinogen or a second oncogenic event. Therefore, selection of transgenic mice with varying transgene copy numbers, or with varying levels of exposure to modulator-inhibiting drugs like niacinamide, will alter the sensitivity of the transgenic mice to the suspected carcinogen or the second oncogenic event. For example, if a higher cyclic AMP level creates a greater sensitivity to a particular carcinogen, transgenic mice with a higher transgene copy number would be particularly useful as a carcinogenicity detection system.

The foregoing specification, including the specific embodiment and examples, is intended to be illustrative of the present invention and is not to be taken as limiting. Numerous other variations and modifications can be effected without departing from the true spirit and scope of the present invention.

What is claimed is:

1. An isolated nucleic acid molecule comprising the promoter from a growth hormone gene operatively linked to a DNA segment encoding cholera toxin.

* * * * *